(12) United States Patent
Reinecke et al.

(10) Patent No.: US 10,174,349 B2
(45) Date of Patent: Jan. 8, 2019

(54) RECOMBINANT CELL PRODUCING 2-HYDROXYISOBUTYRIC ACID

(75) Inventors: Liv Reinecke, Essen (DE); Steffen Schaffer, Herten (DE); Achim Marx, Gelnhausen (DE); Markus Poetter, Muenster (DE); Thomas Haas, Muenster (DE)

(73) Assignee: EVONIK ROEHM GmbH, Darmstadt (DE)

( * ) Notice: Subject to any disclaimer, the term of this patent is extended or adjusted under 35 U.S.C. 154(b) by 78 days.

(21) Appl. No.: 13/001,204

(22) PCT Filed: Apr. 28, 2009

(86) PCT No.: PCT/EP2009/055089
§ 371 (c)(1),
(2), (4) Date: Dec. 23, 2010

(87) PCT Pub. No.: WO2009/156214
PCT Pub. Date: Dec. 30, 2009

(65) Prior Publication Data
US 2011/0171702 A1 Jul. 14, 2011

(30) Foreign Application Priority Data
Jun. 27, 2008 (DE) .................. 10 2008 002 715

(51) Int. Cl.
C12P 7/42 (2006.01)
C12P 7/62 (2006.01)

(52) U.S. Cl.
CPC ............. C12P 7/625 (2013.01); C12P 7/42 (2013.01)

(58) Field of Classification Search
CPC ....................................................... C12P 7/42
See application file for complete search history.

(56) References Cited

U.S. PATENT DOCUMENTS

| | | | |
|---|---|---|---|
| 4,211,846 A * | 7/1980 | Lafferty ................. | 435/141 |
| 5,817,870 A | 10/1998 | Haas et al. | |
| 5,831,121 A | 11/1998 | Haas et al. | |
| 6,472,188 B1 * | 10/2002 | Lee et al. ................. | 435/136 |
| 6,582,943 B1 | 6/2003 | Chauhan et al. | |
| 6,861,540 B2 | 3/2005 | Herwig et al. | |
| 7,157,610 B2 | 1/2007 | Hofen et al. | |
| 7,393,972 B2 | 7/2008 | Pascaly et al. | |
| 7,608,738 B2 | 10/2009 | Herwig et al. | |
| 7,923,225 B2 * | 4/2011 | Mueller et al. ............ | 435/146 |
| 8,022,201 B2 | 9/2011 | Roos et al. | |
| 8,168,841 B2 | 5/2012 | Herwig et al. | |
| 8,216,813 B2 | 7/2012 | Thum et al. | |
| 8,232,333 B2 | 7/2012 | Haeger et al. | |
| 8,404,470 B2 | 3/2013 | Thum et al. | |
| 8,445,720 B2 | 5/2013 | Hannen et al. | |
| 8,486,677 B2 | 7/2013 | Thum et al. | |
| 8,604,227 B2 | 12/2013 | Petrat et al. | |
| 8,796,000 B2 | 8/2014 | Thum et al. | |
| 8,871,862 B2 | 10/2014 | Pawlik et al. | |
| 9,000,223 B2 | 4/2015 | Micoine et al. | |
| 2003/0143703 A1 * | 7/2003 | Lee et al. ................... | 435/135 |
| 2003/0212298 A1 | 11/2003 | Brasse et al. | |
| 2010/0021977 A1 | 1/2010 | May et al. | |
| 2010/0035314 A1 | 2/2010 | Mueller et al. | |
| 2010/0068773 A1 | 3/2010 | Marx et al. | |
| 2010/0167360 A1 | 7/2010 | Thum et al. | |
| 2010/0190219 A1 | 7/2010 | Schaffer et al. | |
| 2010/0190224 A1 | 7/2010 | Poetter et al. | |
| 2010/0210871 A1 | 8/2010 | Kobler et al. | |
| 2010/0261237 A1 | 10/2010 | Verseck et al. | |
| 2010/0291644 A1 | 11/2010 | Marx et al. | |
| 2010/0324257 A1 | 12/2010 | Karau et al. | |
| 2011/0039313 A1 | 2/2011 | Verseck et al. | |
| 2011/0118433 A1 | 5/2011 | Pötter et al. | |
| 2011/0251399 A1 | 10/2011 | Dingerdissen et al. | |
| 2011/0269977 A1 | 11/2011 | Dingerdissen et al. | |
| 2012/0034665 A1 | 2/2012 | Haas et al. | |
| 2012/0041216 A1 | 2/2012 | Sieber et al. | |
| 2012/0071577 A1 | 3/2012 | Pfeffer et al. | |
| 2012/0077932 A1 | 3/2012 | Pfeffer et al. | |
| 2012/0245375 A1 | 9/2012 | Hannen et al. | |
| 2012/0264877 A1 | 10/2012 | Häger et al. | |
| 2013/0035403 A1 | 2/2013 | Schaffer et al. | |
| 2013/0092232 A1 | 4/2013 | Pawlik et al. | |
| 2013/0092233 A1 | 4/2013 | Pawlik et al. | |

(Continued)

FOREIGN PATENT DOCUMENTS

WO    2007 110394    10/2007

OTHER PUBLICATIONS

S.J. Park et al."Biosynthesis of (R)-3-Hydroxyalkanoic Acids by Metabolically Engineered *Escherichia coli*", Applied Biochemistry and Biotechnology vol. 114:373-379 (2004).*
Chinese Office Action dated Aug. 29, 2011, in Patent Application No. 200880010552.3 (with English-language translation).
Copeland, A., et al., Genbank database, CP000577, XP002487016, Feb. 23, 2007.
Copeland, A., et al., Genbank database, ABN77722, Feb. 23, 2007.
U.S. Appl. No. 12/742,318, filed May 11, 2010, US2010/0324257 A1, Karau, et al.

(Continued)

*Primary Examiner* — Rebecca E Prouty
(74) *Attorney, Agent, or Firm* — Oblon, McClelland, Maier & Neustadt, L.L.P.

(57) ABSTRACT

The invention relates to a cell which has been genetically modified so as to be capable of producing more 2-hydroxyisobutyric acid or more polyhydroxyalkanoates containing 2-hydroxyisobutyric acid monomer units than its wild type, characterized in that 2-hydroxyisobutyric acid or polyhydroxyalkanoates containing 2-hydroxyisobutyric acid monomer units are produced via acetoacetyl-coenzyme A as intermediate and 3-hydroxybutyryl-coenzyme A as precursor.

Figure 1:
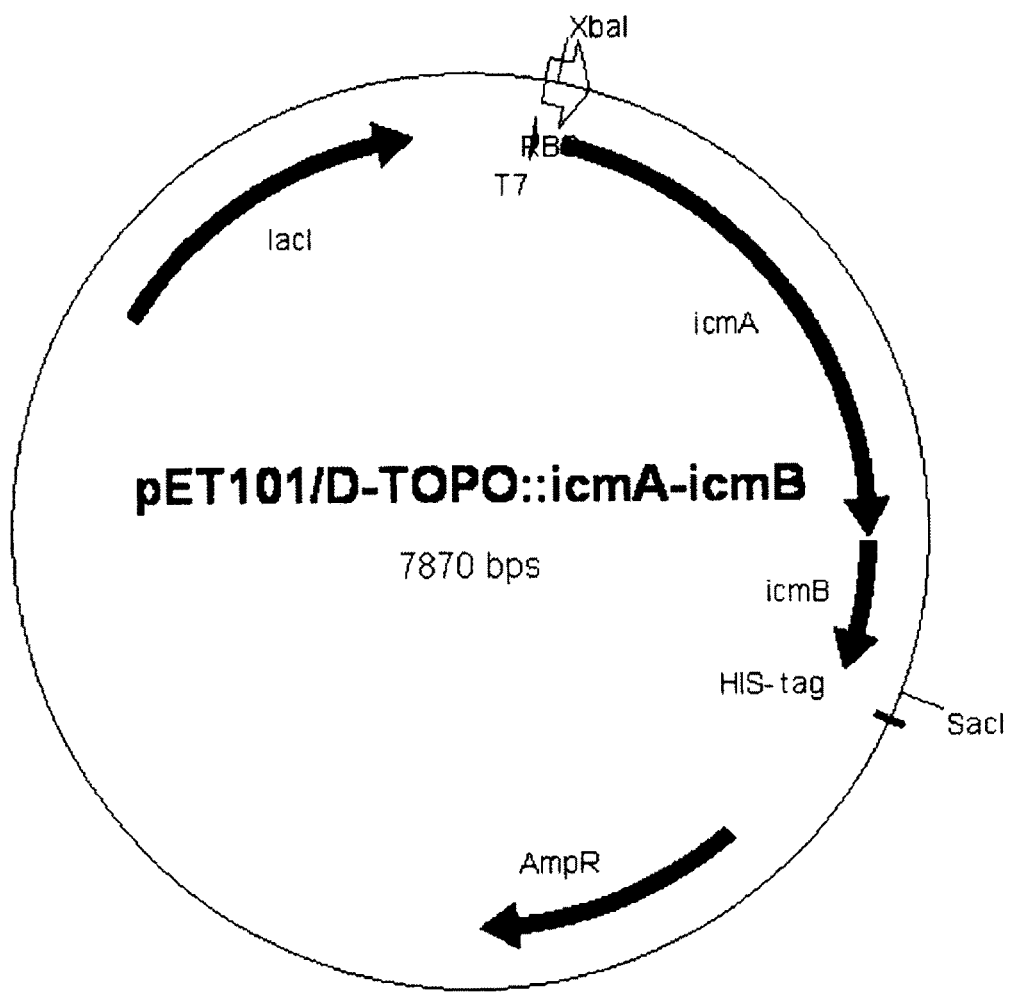

11 Claims, 5 Drawing Sheets
Specification includes a Sequence Listing.

(56) References Cited

U.S. PATENT DOCUMENTS

| | | |
|---|---|---|
| 2013/0130319 A1 | 5/2013 | Schaffer et al. |
| 2013/0165672 A1 | 6/2013 | Klasovsky et al. |
| 2013/0165685 A1 | 6/2013 | Hannen et al. |
| 2013/0171388 A1 | 7/2013 | Pawlik et al. |
| 2013/0183725 A1 | 7/2013 | Poetter et al. |
| 2013/0207050 A1 | 8/2013 | Hermasch et al. |
| 2013/0240799 A1 | 9/2013 | Haeger et al. |
| 2013/0245276 A1 | 9/2013 | Klasovsky et al. |
| 2013/0299750 A1 | 11/2013 | Hermasch et al. |
| 2013/0331580 A1 | 12/2013 | Klasovsky et al. |
| 2014/0141478 A1 | 5/2014 | Schaffer et al. |
| 2014/0178948 A1 | 6/2014 | Schaffer et al. |
| 2014/0199736 A1 | 7/2014 | Köhler et al. |

OTHER PUBLICATIONS

U.S. Appl. No. 12/300,397, filed Dec. 1, 2008, US2010/0190219 A1, Schaffer, et al.
U.S. Appl. No. 12/679,488, filed Mar. 23, 2010, US2010/0261237 A1, Verseck, et al.
U.S. Appl. No. 13/142,883, filed Jun. 30, 2011, US2011/0269977 A1, Dingerdissen, et al.
U.S. Appl. No. 13/140,921, filed Jun. 20, 2011, US2011/0251399 A1, Dingerdissen, et al.
U.S. Appl. No. 13/143,354, filed Jul. 6, 2011, US2012/0041216 A1, Sieber, et al.
U.S. Appl. No. 13/642,412, filed Oct. 19, 2012, Poetter, et al.
U.S. Appl. No. 13/721,481, filed Dec. 20, 2012, Gielen, et al.
U.S. Appl. No. 61/239,634, filed Sep. 3, 2009, Kobler, et al.
U.S. Appl. No. 12/706,512, filed Feb. 16, 2010, US2010/0210871 A1, Kobler, et al.
U.S. Appl. No. 13/141,456, filed Jun. 22, 2011, Schraven, et al.
Ren, O. et al., "Properties of Engineered Poly-3-Hydroxyalkanoates Produced in Recombinant *Escherichia coli* Strains", Applied and Environmental Microbiology, vol. 66, No. 4, pp. 1311-1320, XP 000925369, ISSN: 0099-2240, (Apr. 1, 2000).
Fukui, T. et al., "Engineering of Ralstonia Eutropha for Production of Poly(3-hydroxybutyrate-co-3-hydroxyhexanoate) From Fructose and Solid-State Properties of the Copolymer", Biomacromolecules, vol. 3, No. 3, pp. 618-624, XP 002538853, ISSN: 1525-7797, (May 2002).
Holowach, L. P. et al., "Bacterial Conversion of a Waste Stream Containing Methyl-2-Hydroxyisobutyric Acid to Biodegradable Polyhydroxyalkanoate Polymers", Water-Soluble Polymers, Solution Properties, vol. 575, Chapter 14, pp. 202-211, XP 002957523, ISBN: 978-0-541-23408-9, (Jan. 1, 1994).
Rohwerder, T. et al., "The Alkyl Tert-Butyl Ether Intermediate 2-Hydroxyisobutyrate Is Degraded via a Novel Cobalamin-Dependent Mutase Pathway", Applied and Environmental Microbiology, vol. 72, No. 6, pp. 4128-4135, XP002460829, (Jun. 2006).
International Search Report dated Aug. 11, 2009 in PCT/EP09/055089 filed Apr. 28, 2009.
U.S. Appl. No. 12/593,090, filed Mar. 26, 2010, US2010/0190224 A1, Poetter, et al.
U.S. Appl. No. 12/303,161, filed Apr. 6, 2009, US2010/0068773 A1, Marx, et al.
U.S. Appl. No. 13/054,002, filed Jan. 13, 2011, Haas, et al.
U.S. Appl. No. 12/602,593, filed Mar. 2010, US2010/0291644 A1, Marx, et al.
U.S. Appl. No. 13/002,519, filed Jan. 4, 2011, Haas, et al.
U.S. Appl. No. 12/294,308, filed Sep. 24, 2008, US2010/0035314 A1, Mueller, et al.
U.S. Appl. No. 12/950,752, filed Nov. 19, 2010, Mueller, et al.
U.S. Appl. No. 12/441,145, filed Mar. 13, 2009, US2010/0021977 A1, May, et al.
U.S. Appl. No. 13/500,041, filed Apr. 3, 2012, Reinecke, et al.
U.S. Appl. No. 13/263,761, filed Oct. 10, 2011, US2012/0034665 A1, Haas, et al.
U.S. Appl. No. 12/943,145, filed Nov. 10, 2010, US2011/0118433 A1, Pötter, et al.
U.S. Appl. No. 13/820,803, filed Mar. 5, 2013, US2013/0165672 A1, Klasovsky, et al.
U.S. Appl. No. 14/000,067, filed Aug. 16, 2013, Erhardt, et al.
U.S. Appl. No. 14/000,028, filed Aug. 16, 2013, Erhardt, et al.
U.S. Appl. No. 14/363,178, filed Jun. 5, 2014, Haas, et al.
U.S. Appl. No. 14/363,165, filed Jun. 5, 2014, Pfeffer, et al.
U.S. Appl. No. 14/367,610, filed Jun. 20, 2014, Haas, et al.
U.S. Appl. No. 14/373,089, filed Jul. 18, 2014, Engel, et al.
U.S. Appl. No. 14/380,483, filed Aug. 22, 2014, Schiemann, et al.
U.S. Appl. No. 14/238,248, filed Feb. 11, 2014, US2014/0199736 A1, Köhler, et al.
U.S. Appl. No. 12/354,256, filed Jan. 15, 2009, US2010/0167360 A1, Thum, et al.
U.S. Appl. No. 10/396,688, filed Mar. 26, 2003, US2003/0212298 A1, Brasse, et al.
U.S. Appl. No. 14/110,450, filed Oct. 8, 2013, Klasovsky, et al.
U.S. Appl. No. 14/126,607, filed Dec. 16, 2013, Haas, et al.
U.S. Appl. No. 14/238,576, filed Feb. 12, 2014, Schaffer, et al.
U.S. Appl. No. 14/238,591, filed Feb. 12, 2014, Schaffer, et al.
U.S. Appl. No. 14/233,505, filed Jan. 17, 2014, Poetter, et al.
U.S. Appl. No. 14/237,121, filed Feb. 4, 2014, Haas, et al.
U.S. Appl. No. 12/517,923, filed Jun. 5, 2009, US2011/0039313 A1, Verseck, et al.
U.S. Appl. No. 13/764,996, filed Feb. 12, 2013, US2013/0183725 A1, Poetter, et al.
U.S. Appl. No. 13/806,555, filed Mar. 11, 2013, US2013/0165685 A1, Hannen, et al.
U.S. Appl. No. 13/812,625, filed Jan. 28, 2013, US2013/0130319 A1, Schaffer, et al.
U.S. Appl. No. 13/989,419, filed May 24, 2013, US2013/0245276 A1, Klasovsky, et al.
U.S. Appl. No. 14/000,400, filed Aug. 20, 2013, US2013/0331580 A1, Klasovsky, et al.
U.S. Appl. No. 13/424,548, filed Mar. 20, 2012, US2012/0245375 A1, Hannen, et al.
U.S. Appl. No. 13/649,616, filed Oct. 11, 2012, US2013/0092233 A1, Pawlik, et al.
U.S. Appl. No. 14/384,301, filed Sep. 10, 2014, Schaffer, et al.
U.S. Appl. No. 14/390,133, filed Oct. 2, 2014, Hennemann, et al.
U.S. Appl. No. 14/395,666, filed Oct. 20, 2014, Haas, et al.
U.S. Appl. No. 14/405,050, filed Dec. 2, 2014, Haas, et al.
U.S. Appl. No. 14/400,379, filed Nov. 11, 2014, Haas, et al.
U.S. Appl. No. 13/376,757, filed Dec. 7, 2011, US2012/0077932 A1, Pfeffer, et al.
U.S. Appl. No. 13/375,664, filed Dec. 1, 2011, US2012/0071577 A1, Pfeffer, et al.
U.S. Appl. No. 13/882,689, filed Jul. 15, 2013, US2013/0299750 A1, Hermasch, et al.
U.S. Appl. No. 14/132,473, filed Dec. 18, 2013, US2014/0178948 A1, Schaffer, et al.
U.S. Appl. No. 14/425,180, filed Mar. 2, 2015, Ortelt, et al.
U.S. Appl. No. 14/435,339, filed Apr. 13, 2015, Engel, et al.
U.S. Appl. No. 14/763,378, filed Jul. 24, 2015, Haas, et al.
Office Action dated Jun. 15, 2016 in Chinese Patent Application No. 200980124253.7 (with English translation).
Kazunori Taguchi et al., "Metabolic Pathways and Engineering of PHA Biosynthesis", Biological Systems and Biotechnological Production, Biopolymer vol. 3a: Polyesters I, Jul. 31, 2004, pp. 229-233, 281-285 9 (with English language translation).
"4 Microbial Water-insoluble Aliphatic Polyesters (PHA)", Biological Systems and Biotechnological Production, , Biopolymer vol. 3a: Polyesters I, Jul. 31, 2004, pp. 112-113 (with English language translation).
"2 Biosynthesis of PHAs", Biological Systems and Biotechnological Production, Biopolymer vol. 3a: Polyesters I, Jul. 31, 2004, p. 115 (with English language translation).
"4 Microbial Water-insoluble Aliphatic Polyesters (PHA)", Biological Systems and Biotechnological Production, , Biopolymer vol. 3a: Polyesters I, Jul. 31, 2004, pp. 117-120 (with English language translation).
Kalousek S and Lubitz W. "High-level poly(beta-hydroxybutyrate) production in recombinant *Escherichia coli* in sugar-free, complex medium", Can J Microbiol. 1995;41 Suppl 1:216-21.

(56) References Cited

OTHER PUBLICATIONS

Hai-Jun Gao et al, "Enhanced production of D-(-)-3-hydroxybutric acid by recombinant *Escherichia coli*", FEMS Microbiology letters 213 (2002), 59-65.
U.S. Appl. No. 13/494,082, filed Jun. 12, 2012, US2012/0264877 A1, Häger et al.
U.S. Appl. No. 13/882,799, filed May 1, 2013, US2013/0207050 A1, Hermasch et al.
U.S. Appl. No. 13/729,280, filed Dec. 28, 2012, US2013/0171388 A1, Pawlik et al.
U.S. Appl. No. 13/804,328, filed Mar. 14, 2013, US2013/0240799 A1, Haeger et al.
U.S. Appl. No. 13/649,379, filed Oct. 11, 2012, US2013/0092232 A1, Pawlik et al.
U.S. Appl. No. 14/077,750, filed Nov. 12, 2013, US2014/0141478 A1, Schaffer et al.
U.S. Appl. No. 14/649,414, filed Jun. 3, 2015, Schaffer et al.
U.S. Appl. No. 13/509,716, filed May 14, 2012, US2013/0035403 A1, Schaffer, et al.

\* cited by examiner

SEQUENCE LISTING

```
<160> NUMBER OF SEQ ID NOS: 8

<210> SEQ ID NO 1
<211> LENGTH: 7870
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
caaggagatg gcgcccaaca gtcccccggc cacggggcct gccaccatac ccacgccgaa      60
acaagcgctc atgagcccga agtggcgagc ccgatcttcc ccatcggtga tgtcggcgat     120
ataggcgcca gcaaccgcac ctgtggcgcc ggtgatgccg gccacgatgc gtccggcgta     180
gaggatcgag atctcgatcc cgcgaaatta atacgactca ctatagggga attgtgagcg     240
gataacaatt cccctctaga aataattttg tttaacttta agaaggaatt caggagccct     300
tcaccatgac ctggcttgag ccgcagataa agtcccaact ccaatcggag cgcaaggact     360
gggaagcgaa cgaagtcggc gccttcttga agaaggcccc cgagcgcaag gagcagttcc     420
acacgatcgg ggacttcccg gtccagcgca cctacaccgc tgccgacatc gccgacacgc     480
cgctggagga catcggtctt ccggggcgct acccgttcac gcgcgggccc tacccgacga     540
tgtaccgcag ccgcacctgg acgatgcgcc agatcgccgg cttcggcacc ggcgaggaca     600
ccaacaagcg cttcaagtat ctgatcgcgc agggccagac cggcatctcc accgacttcg     660 acatgccccac gctgatgggc tacgactccg accacccgat gagcgacggc gaggtcggcc     720
gcgagggcgt ggcgatcgac acgctggccg acatggaggc gctgctggcc gacatcgacc     780
tcgagaagat ctcggtctcg ttcacgatca acccgagcgc ctggatcctg ctcgcgatgt     840
acgtggcgct cggcgagaag cgcggctacg acctgaacaa gctgtcgggc acggtgcagg     900
ccgacatcct gaaggagtac atggcgcaga aggagtacat ctacccgatc gcgccgtcgg     960
tgcgcatcgt gcgcgacatc atcacctaca gcgcgaagaa cctgaagcgc tacaacccga    1020
tcaacatctc gggctaccac atcagcgagg ccggctcctc gccgctccag gaggcggcct    1080
tcacgctggc caacctgatc acctacgtga acggtgac gaagaccggt atgcacgtcg      1140
acgaattcgc gccgcggttg gccttcttct tcgtgtcgca aggtgacttc ttcgaggagg    1200
```

```
tcgcgaagtt ccgcgccctg cgccgctgct acgcgaagat catgaaggag cgcttcggtg    1260
caagaaatcc ggaatcgatg cggttgcgct tccactgtca gaccgcggcg gcgacgctga    1320
ccaagccgca gtacatggtc aacgtcgtgc gtacgtcgct gcaggcgctg tcggccgtgc    1380
tcggcggcgc gcagtcgctg cacaccaacg gctacgacga agccttcgcg atcccgaccg    1440
aggatgcgat gaagatggcg ctgcgcacgc agcagatcat tgccgaggag agtggtgtcg    1500
ccgacgtgat cgaccgctg gtggcagct actacgtcga ggcgctgacc accgagtacg    1560
agaagaagat cttcgagatc ctcgaggaag tcgagaagcg cggtggcacc atcaagctga    1620
tcgagcaggg ctggttccag aagcagattg cggacttcgc ttacgagacc cgcgctgcgca    1680 agcagtccgg ccagaagccg gtgatcgggg tgaaccgctt cgtcgagaac gaagaggacg    1740
tcaagatcga gatccacccg tacgacaaca cgacggccga acgccagatt tcccgcacgc    1800
gccgcgttcg cgccgagcgc gacgaggcca aggtgcaagc gatgctcgac caactggtgg    1860
ctgtcgccaa ggacgagtcc cagaacctga tgccgctgac catcgaactg gtgaaggccg    1920
gcgcaacgat gggggacatc gtcgagaagc tgaagggat ctggggtacc taccgcgaga    1980
cgccggtctt ctgagcagga agcttccac catggaccaa atcccgatcc gcgttcttct    2040
cgccaaagtc ggcctcgacg gccatgaccg aggcgtcaag gtcgtcgctc gcgcgctgcg    2100
cgacgccggc atggacgtca tctactccgg ccttcatcgc acgccgaag aggtggtcaa    2160 caccgccatc caggaagacg tggacgtgct gggtgtaagc ctcctgtccg gcgtgcagct    2220
cacggtcttc cccaagatct tcaagctcct ggacgagaga ggcgctggcg acttgatcgt    2280
gatcgccggt ggcgtgatgc cggacgagga cgccgcggcc atccgcaagc tcggcgtgcg    2340
cgaggtgcta ctgcaggaca cgcccccgca ggccatcatc gactcgatcc gctccttggt    2400
cgccgcgcgc ggcgcccgct gaaagggcga gctcaattcg aagcttgaag gtaagcctat    2460
ccctaaccct ctcctcggtc tcgattctac gcgtaccggt catcatcacc atcaccattg    2520
agtttgatcc ggctgctaac aaagcccgaa aggaagctga gttggctgct gccaccgctg    2580
agcaataact agcataaccc cttggggcct ctaaacgggt cttgaggggt tttttgctga    2640
aaggaggaac tatatccgga tatcccgcaa gaggcccggc agtaccggca taaccaagcc    2700
tatgcctaca gcatccaggg tgacggtgcc gaggatgacg atgagcgcat tgttagattt    2760
catacacggt gcctgactgc gttagcaatt taactgtgat aaactaccgc attaaagctt    2820
atcgatgata agctgtcaaa catgagaatt aattcttgaa gacgaaaggg cctcgtgata    2880
cgcctatttt tataggttaa tgtcatgata ataatggttt cttagacgtc aggtggcact    2940
tttcggggaa atgtgcgcgg aacccctatt tgtttatttt tctaaataca ttcaaatatg    3000
tatccgctca tgagacaata accctgataa atgcttcaat aatattgaaa aggaagagt    3060 atgagtattc aacatttccg tgtcgccctt attccctttt ttgcggcatt ttgccttcct    3120
gtttttgctc acccagaaac gctggtgaaa gtaaaagatg ctgaagatca gttgggtgca    3180
cgagtgggtt acatcgaact ggatctcaac agcggtaaga tccttgagag ttttcgcccc    3240
gaagaacgtt ttccaatgat gagcactttt aaagttctgc tatgtggcgc ggtattatcc    3300
cgtgttgacg ccgggcaaga gcaactcggt cgccgcatac actattctca gaatgacttg    3360
gttgagtact caccagtcac agaaaagcat cttacggatg gcatgacagt aagagaatta    3420
tgcagtgctg ccataaccat gagtgataac actgcggcca acttacttct gacaacgatc    3480
ggaggaccga aggagctaac cgcttttttg cacaacatgg gggatcatgt aactcgcctt    3540
```

```
gatcgttggg aaccggagct gaatgaagcc ataccaaacg acgagcgtga caccacgatg    3600
cctgcagcaa tggcaacaac gttgcgcaaa ctattaactg gcgaactact tactctagct    3660
tcccggcaac aattaataga ctggatggag gcggataaag ttgcaggacc acttctgcgc    3720
tcggcccttc cggctggctg gtttattgct gataaatctg gagccggtga gcgtgggtct    3780
cgcggtatca ttgcagcact ggggccagat ggtaagccct cccgtatcgt agttatctac    3840
acgacgggga gtcaggcaac tatggatgaa cgaaatagac agatcgctga gataggtgcc    3900
tcactgatta agcattggta actgtcagac caagtttact catatatact ttagattgat    3960
ttaaaacttc attttaatt taaaaggatc taggtgaaga tcctttttga taatctcatg    4020
accaaaatcc cttaacgtga gttttcgttc cactgagcgt cagaccccgt agaaaagatc    4080
aaaggatctt cttgagatcc ttttttttctg cgcgtaatct gctgcttgca acaaaaaaaa    4140
ccaccgctac cagcggtggt ttgtttgccg gatcaagagc taccaactct ttttccgaag    4200
gtaactggct tcagcagagc gcagatacca aatactgtcc ttctagtgta gccgtagtta    4260
ggccaccact tcaagaactc tgtagcaccg cctacatacc tcgctctgct aatcctgtta    4320
ccagtggctg ctgccagtgg cgataagtcg tgtcttaccg ggttggactc aagacgatag    4380
ttaccggata aggcgcagcg gtcgggctga acggggggtt cgtgcacaca gcccagcttg    4440
gagcgaacga cctacaccga actgagatac ctacagcgtg agctatgaga aagcgccacg    4500
cttcccgaag ggagaaaggc ggacaggtat ccggtaagcg gcagggtcgg aacaggagag    4560
cgcacgaggg agcttccagg gggaaacgcc tggtatcttt atagtcctgt cgggtttcgc    4620
cacctctgac ttgagcgtcg atttttgtga tgctcgtcag ggggggcgag cctatggaaa    4680
aacgccagca acgcggcctt tttacggttc ctggcctttt gctggccttt tgctcacatg    4740
ttctttcctg cgttatcccc tgattctgtg gataaccgta ttaccgcctt tgagtgagct    4800
gataccgctc gccgcagccg aacgaccgag cgcagcgagt cagtgagcga ggaagcggaa    4860
gagcgcctga tgcggtattt tctccttacg catctgtgcg gtatttcaca ccgcaatggt    4920
gcactctcag tacaatctgc tctgatgccg catagttaag ccagtataca ctccgctatc    4980
gctacgtgac tgggtcatgg ctgcgccccg acacccgcca cacccgctg acgcgccctg    5040 acgggcttgt ctgctcccgg catccgctta cagacaagct gtgaccgtct ccgggagctg    5100
catgtgtcag aggttttcac cgtcatcacc gaaacgcgcg aggcagctgc ggtaaagctc    5160
atcagcgtgg tcgtgaagcg attcacagat gtctgcctgt tcatccgcgt ccagctcgtt    5220
gagtttctcc agaagcgtta atgtctggct tctgataaag cgggccatgt taagggcggt    5280
tttttcctgt ttggtcactg atgcctccgt gtaagggggga tttctgttca tgggggtaat    5340
gataccgatg aaacgagaga ggatgctcac gatacgggtt actgatgatg aacatgcccg    5400
gttactggaa cgttgtgagg gtaaacaact ggcggtatgg atgcggcggg accagagaaa    5460
aatcactcag ggtcaatgcc agcgcttcgt taatacagat gtaggtgttc cacagggtag    5520
ccagcagcat cctgcgatgc agatccggaa cataatggtg cagggcgctg acttccgcgt    5580
ttccagactt tacgaaacac ggaaaccgaa gaccattcat gttgttgctc aggtcgcaga    5640
cgttttgcag cagcagtcgc ttcacgttcg ctcgcgtatc ggtgattcat tctgctaacc    5700
agtaaggcaa ccccgccagc ctagccgggt cctcaacgac aggagcacga tcatgcgcac    5760
ccgtggccag gacccaacgc tgcccgagat gcgccgcgtg cggctgctgg agatggcgga    5820
cgcgatggat atgttctgcc aagggttggt ttgcgcattc acagttctcc gcaagaattg    5880
attggctcca attcttggag tggtgaatcc gttagcgagg tgccgccggc ttccattcag    5940
```

```
gtcgaggtgg cccggctcca tgcaccgcga cgcaacgcgg ggaggcagac aaggtatagg    6000
gcggcgccta caatccatgc caacccgttc catgtgctcg ccgaggcggc ataaatcgcc    6060
gtgacgatca gcggtccaat gatcgaagtt aggctggtaa gagccgcgag cgatccttga    6120
agctgtccct gatggtcgtc atctacctgc ctggacagca tggcctgcaa cgcgggcatc    6180
ccgatgccgc cggaagcgag aagaatcata tggggaagg  ccatccagcc tcgcgtcgcg    6240
aacgccagca agacgtagcc cagcgcgtcg gccgccatgc cggcgataat ggcctgcttc    6300
tcgccgaaac gtttggtggc gggaccagtg acgaaggctt gagcgagggc gtgcaagatt    6360
ccgaataccg caagcgacag gccgatcatc gtcgcgctcc agcgaaagcg gtcctcgccg    6420
aaaatgaccc agagcgctgc cggcacctgt cctacgagtt gcatgataaa gaagacagtc    6480
ataagtgcgg cgacgatagt catgcccgc  gcccaccgga aggagctgac tgggttgaag    6540
gctctcaagg gcatcggtcg agatcccggt gcctaatgag tgagctaact tacattaatt    6600
gcgttgcgct cactgcccgc tttccagtcg ggaaacctgt cgtgccagct gcattaatga    6660
atcggccaac gcgcggggag aggcggtttg cgtattgggc gccagggtgg ttttctttt     6720 caccagtgag acgggcaaca gctgattgcc cttcaccgcc tggccctgag agagttgcag    6780
caagcggtcc acgctggttt gccccagcag gcgaaaatcc tgtttgatgg tggttaacgg    6840
cgggatataa catgagctgt cttcggtatc gtcgtatccc actaccgaga tatccgcacc    6900
aacgcgcagc ccggactcgg taatggcgcg cattgcgccc agcgccatct gatcgttggc    6960
aaccagcatc gcagtgggaa cgatgccctc attcagcatt tgcatggttt gttgaaaacc    7020
ggacatggca ctccagtcgc cttcccgttc cgctatcggc tgaatttgat tgcgagtgag    7080
atatttatgc cagccagcca gacgcagacg cgccgagaca gaacttaatg ggcccgctaa    7140
cagcgcgatt tgctggtgac ccaatgcgac cagatgctcc acgcccagtc gcgtaccgtc    7200
ttcatgggag aaaataatac tgttgatggg tgtctggtca gagacatcaa gaaataacgc    7260
cggaacatta gtgcaggcag cttccacagc aatggcatcc tggtcatcca gcggatagtt    7320
aatgatcagc ccactgacgc gttgcgcgag aagattgtgc accgccgctt tacaggcttc    7380
gacgccgctt cgttctacca tcgacaccac cacgctggca cccagttgat cggcgcgaga    7440
tttaatcgcc gcgacaattt gcgacggcgc gtgcagggcc agactggagg tggcaacgcc    7500
aatcagcaac gactgtttgc ccgccagttg ttgtgccacg cggttgggaa tgtaattcag    7560
ctccgccatc gccgcttcca cttttttcccg cgttttcgca gaaacgtggc tggcctggtt    7620
caccacgcgg gaaacggtct gataagagac accggcatac tctgcgacat cgtataacgt    7680
tactggtttc acattcacca ccctgaattg actctcttcc gggcgctatc atgccatacc    7740
gcgaaaggtt ttgcgccatt cgatggtgtc cgggatctcg acgctctccc ttatgcgact    7800
cctgcattag gaagcagccc agtagtaggt tgaggccgtt gagcaccgcc gccgcaagga    7860
atggtgcatg                                                            7870
```

<210> SEQ ID NO 2  
<211> LENGTH: 7296  
<212> TYPE: DNA  
<213> ORGANISM: Artificial Sequence  
<220> FEATURE:  
<223> OTHER INFORMATION: Description of Artificial Sequence: Synthetic polynucleotide

<400> SEQUENCE: 2

```
accttcggga gcgcctgaag cccgttctgg acgcccctggg gccgttgaat cgggatatgc    60
```

```
aggccaaggc cgccgcgatc atcaaggccg tgggcgaaaa gctgctgacg gaacagcggg     120
aagtccagcg ccagaaacag gcccagcgcc agcaggaacg cgggcgcgca catttccccg     180
aaaagtgcca cctgggatga atgtcagcta ctgggctatc tggacaaggg aaaacgcaag     240
cgcaaagaga aagcaggtag cttgcagtgg gcttacatgg cgatagctag actgggcggt     300
tttatggaca gcaagcgaac cggaattgcc agctggggcg ccctctggta aggttgggaa     360
gccctgcaaa gtaaactgga tggctttctt gccgccaagg atctgatggc caggggatc     420 aagatctgat caagagacag gatgaggatc gtttcgcatg attgaacaag atggattgca     480
cgcaggttct ccggccgctt gggtggagag gctattcggc tatgactggg cacaacagac     540
aatcggctgc tctgatgccg ccgtgttccg gctgtcagcg caggggcgcc cggttctttt     600
tgtcaagacc gacctgtccg gtgccctgaa tgaactgcag gacgaggcag cgcggctatc     660
gtggctggcc acgacgggcg ttccttgcgc agctgtgctc gacgttgtca ctgaagcggg     720
aagggactgg ctgctattgg gcgaagtgcc ggggcaggat ctcctgtcat ctcaccttgc     780
tcctgccgag aaagtatcca tcatggctga tgcaatgcgg cggctgcata cgcttgatcc     840
ggctacctgc ccattcgacc accaagcgaa acatcgcatc gagcgagcac gtactcggat     900
ggaagccggt cttgtcgatc aggatgatct ggacgaagag catcaggggc tcgcgccagc     960
cgaactgttc gccaggctca aggcgcgcat gcccgacggc gaggatctcg tcgtgaccca     1020
tggcgatgcc tgcttgccga atatcatggt ggaaaatggc cgcttttctg gattcatcga     1080
ctgtggccgg ctgggtgtgg cggaccgcta tcaggacata gcgttggcta cccgtgatat     1140
tgctgaagag cttggcggcg aatgggctga ccgcttcctc gtgctttacg gtatcgccgc     1200
tcccgattcg cagcgcatcg ccttctatcg ccttcttgac gagttcttct gagcgggact     1260
ctggggttcg aaatgaccga ccaagcgacg cccaacctgc catcacgaga tttcgattcc     1320
accgccgcct tctatgaaag gttgggcttc ggaatcgttt tccgggacgc cggctggatg     1380
atcctccagc gcggggatct catgctggag ttcttcgccc accccatgg gcaaatatta     1440 tacgcaaggc gacaaggtgc tgatgccgct ggcgattcag gttcatcatg ccgtttgtga     1500
tggcttccat gtcggcagaa tgcttaatga attacaacag ttttatgca tgcgcccaat     1560 acgcaaaccg cctctccccg cgcgttggcc gattcattaa tgcagctggc acgacaggtt     1620
tcccgactgg aaagcgggca gtgagcgcaa cgcaattaat gtgagttagc tcactcatta     1680
ggcaccccag gctttacact ttatgcttcc ggctcgtatg ttgtgtggaa ttgtgagcgg     1740
ataacaattt cacacaggaa acagctatga ccatgattac gccaagcgcg caattaaccc     1800
tcactaaagg gaacaaaagc tgggtaccgg gccccccctc gaggtcgacg gtatcgataa     1860
gcttgatatc gaattcctgc agcccggggg atccactagt tctagaaata attttgttta     1920
actttaagaa ggaattcagg agcccttcac catgacctgg cttgagccgc agataaagtc     1980
ccaactccaa tcggagcgca aggactggga agcgaacgaa gtcggcgcct tcttgaagaa     2040
ggcccccgag cgcaaggagc agttccacac gatcgggac ttcccggtcc agcgcaccta     2100
caccgctgcc gacatcgccg acacgccgct ggaggacatc ggtcttccgg ggcgctaccc     2160
gttcacgcgc gggccctacc cgacgatgta ccgcagccgc acctggacga tgcgccagat     2220
cgccggcttc ggcaccggcg aggacaccaa caagcgcttc aagtatctga tcgcgcaggg     2280
ccagaccgga atctccaccg acttcgacat gcccacgctg atgggctacg actccgacca     2340
cccgatgagc gacggcgagg tcggccgcga gggcgtggcg atcgacacgc tggccgacat     2400
```

```
ggaggcgctg ctggccgaca tcgacctcga aagatctccg gtctcgttca cgatcaaccc    2460
gagcgcctgg atcctgctcg cgatgtacgt ggcgctcggc gagaagcgcg gctacgacct    2520
gaacaagctg tcgggcacgg tgcaggccga catcctgaag gagtacatgg cgcagaagga    2580
gtacatctac ccgatcgcgc cgtcggtgcg catcgtgcgc gacatcatca cctacagcgc    2640
gaagaacctg aagcgctaca acccgatcaa catctcgggc taccacatca gcgaggccgg    2700
ctcctcgccg ctccaggagg cggccttcac gctggccaac ctgatcacct acgtgaacga    2760
ggtgacgaag accggtatgc acgtcgacga attcgcgccg cggttggcct tcttcttcgt    2820
gtcgcaaggt gacttcttcg aggaggtcgc gaagttccgc gccctgcgcc gctgctacgc    2880
gaagatcatg aaggagcgct tcggtgcaag aaatccggaa tcgatgcggt tgcgcttcca    2940
ctgtcagacc gcggcggcga cgctgaccaa gccgcagtac atggtcaacg tcgtgcgtac    3000
gtcgctgcag gcgctgtcgg ccgtgctcgg cggcgcgcag tcgctgcaca ccaacggcta    3060
cgacgaagcc ttcgcgatcc cgaccgagga tgcgatgaag atggcgctgc gcacgcagca    3120
gatcattgcc gaggagagtg tgtcgccga cgtgatcgac ccgctgggtg gcagctacta    3180
cgtcgaggcg ctgaccaccg agtacgagaa gaagatcttc gagatcctcg aggaagtcga    3240
gaagcgcggt ggcaccatca agctgatcga gcagggctgg ttccagaagc agattgcgga    3300
cttcgcttac gagaccgcgc tgcgcaagca gtccggccag aagccggtga tcggggtgaa    3360
ccgcttcgtc gagaacgaag aggacgtcaa gatcgagatc cacccgtacg acaacacgac    3420
ggccgaacgc cagatttccc gcacgcgccg cgttcgcgcc gagcgcgacg aggccaaggt    3480
gcaagcgatg ctcgaccaac tggtggctgt cgccaaggac gagtcccaga acctgatgcc    3540
gctgaccatc gaactggtga aggccggcgc aacgatgggg gacatcgtcg agaagctgaa    3600
ggggatctgg ggtacctacc gcgagacgcc ggtcttctga gcaggaagct tcccaccatg    3660
gaccaaatcc cgatccgcgt tcttctcgcc aaagtcggcc tcgacggcca tgaccgaggc    3720
gtcaaggtcg tcgctcgcgc gctgcgcgac gccggcatgg acgtcatcta ctccggcctt    3780
catcgcacgc ccgaagaggt ggtcaacacc gccatccagg aagacgtgga cgtgctgggt    3840
gtaagcctcc tgtccggcgt gcagctcacg gtcttcccca agatcttcaa gctcctggac    3900
gagagaggcg ctggcgactt gatcgtgatc gccggtggcg tgatgccgga cgaggacgcc    3960
gcggccatcc gcaagctcgg cgtgcgcgag gtgctactgc aggacacgcc cccgcaggcc    4020
atcatcgact cgatccgctc cttggtcgcc gcgcgcggcg cccgctgaaa gggcgagctc    4080
tccaattcgc cctatagtga gtcgtattac gcgcgctcac tggccgtcgt tttacaacgt    4140
cgtgactggg aaaaccctgg cgttacccaa cttaatcgcc ttgcagcaca tccccctttc    4200
gccagctggc gtaatagcga agaggcccgc accgatcgcc cttcccaaca gttgcgcagc    4260
ctgaatggcg aatggaaatt gtaagcgtta atattttgtt aaaattcgcg ttaaattttt    4320
gttaaatcag ctcattttt aaccaatagg ccgactgcga tgagtggcag gcgggggcgt    4380
aattttttta aggcagttat tggtgccctt aaacgcctgg tgctacgcct gaataagtga    4440
taataagcgg atgaatggca gaaattcgaa agcaaattcg acccggtcgt cggttcaggg    4500
cagggtcgtt aaatagccgc ttatgtctat tgctggttta ccggtttatt gactaccgga    4560
agcagtgtga ccgtgtgctt ctcaaatgcc tgaggccagt ttgctcaggc tctccccgtg    4620
gaggtaataa ttgacgatat gatcattat tctgcctccc agagcctgat aaaaacggtg    4680
aatccgttag cgaggtgccg ccggcttcca ttcaggtcga ggtggcccgg ctccatgcac    4740
cgcgacgcaa cgcggggagg cagacaaggt atagggcggc gaggcggcta cagccgatag    4800
```

```
tctggaacag cgcacttacg ggttgctgcg caacccaagt gctaccggcg cggcagcgtg    4860
acccgtgtcg gcggctccaa cggctcgcca tcgtccagaa acacggctc atcgggcatc     4920 ggcaggcgct gctgcccgcg ccgttccat tcctccgttt cggtcaaggc tggcaggtct      4980
ggttccatgc ccggaatgcc gggctggctg gcggctcct cgccggggcc ggtcggtagt      5040
tgctgctcgc ccggatacag ggtcgggatg cggcgcaggt cgccatgccc caacagcgat    5100
tcgtcctggt cgtcgtgatc aaccaccacg gcggcactga acaccgacag cgcaactgg     5160 tcgcggggct ggccccacgc cacgcggtca ttgaccacgt aggccgacac ggtgccgggg    5220
ccgttgagct tcacgacgga gatccagcgc tcggccacca agtccttgac tgcgtattgg    5280
accgtccgca agaacgtcc gatgagcttg gaaagtgtct tctggctgac caccacggcg     5340
ttctggtggc ccatctgcgc cacgaggtga tgcagcagca ttgccgccgt gggtttcctc    5400
gcaataagcc cggcccacgc ctcatgcgct ttgcgttccg tttgcaccca gtgaccgggc    5460
ttgttcttgg cttgaatgcc gatttctctg gactgcgtgg ccatgcttat ctccatgcgg    5520
tagggtgccg cacggttgcg gcaccatgcg caatcagctg caactttcg gcagcgcgac     5580 aacaattatg cgttgcgtaa aagtggcagt caattacaga ttttctttaa cctacgcaat    5640
gagctattgc gggggtgcc gcaatgagct gttgcgtacc ccccttttt aagttgttga      5700 tttttaagtc tttcgcattt cgccctatat ctagttcttt ggtgcccaaa gaagggcacc    5760 cctgcgggt tcccccacgc cttcggcgcg gctcccccctc cggcaaaaag tggcccctcc    5820
ggggcttgtt gatcgactgc gcggccttcg gccttgccca aggtggcgct gcccccttgg    5880 aaccccgca ctcgccgccg tgaggctcgg ggggcaggcg ggcgggcttc gccttcgact     5940
gcccccactc gcataggctt gggtcgttcc aggcgcgtca aggccaagcc gctgcgcggt    6000
cgctgcgcga gccttgaccc gccttccact tggtgtccaa ccggcaagcg aagcgcgcag   6060
gccgcaggcc ggaggctttt ccccagagaa aattaaaaaa attgatgggg caaggccgca   6120
ggccgcgcag ttggagccgg tgggtatgtg gtcgaaggct gggtagccgg tgggcaatcc    6180
ctgtggtcaa gctcgtgggc aggcgcagcc tgtccatcag cttgtccagc agggttgtcc    6240
acgggccgag cgaagcgagc cagccggtgg ccgctcgcgg ccatcgtcca catatccacg    6300
ggctggcaag ggagcgcagc gaccgcgcag ggcgaagccc ggagagcaag cccgtagggc    6360
gccgcagccg ccgtaggcgg tcacgacttt gcgaagcaaa gtctagtgag tatactcaag   6420
cattgagtgg cccgccggag gcaccgcctt gcgctgcccc cgtcgagccg gttggacacc    6480
aaaagggagg ggcaggcatg gcggcatacg cgatcatgcg atgcaagaag ctggcgaaaa    6540
tgggcaacgt ggcggccagt ctcaagcacg cctaccgcga gcgcgagacg cccaacgctg    6600
acgccagcag gacgccagag aacgagcact gggcggccag cagcaccgat gaagcgatgg    6660
gccgactgcg cgagttgctg ccagagaagc ggcgcaagga cgctgtgttg gcggtcgagt    6720
acgtcatgac ggccagcccg gaatggtgga agtcggccag ccaagaacag caggcggcgt    6780
tcttcgagaa ggcgcacaag tggctggcgg acaagtacgg ggcggatcgc atcgtgacgg    6840
ccagcatcca ccgtgacgaa accagcccgc acatgaccgc gttcgtggtg ccgctgacgc    6900
aggacggcag gctgtcggcc aaggagttca tcggcaacaa agcgcagatg acccgcgacc    6960
agaccacgtt tgcggccgct gtggccgatc tagggctgca acggggcatc gagggcagca    7020
aggcacgtca cacgcgcatt caggcgttct acgaggccct ggagcggcca ccagtgggcc    7080
acgtcaccat cagcccgcaa gcggtcgagc cacgcgccta tgcaccgcag ggattggccg    7140
```

-continued

```
aaaagctggg aatctcaaag cgcgttgaga cgccggaagc cgtggccgac cggctgacaa     7200
aagcggttcg gcaggggtat gagcctgccc tacaggccgc cgcaggagcg cgtgagatgc     7260
gcaagaaggc cgatcaagcc caagagacgg cccgag                                7296
```

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3

```
caccatgacc tggcttgagc cgcag                                              25
```

<210> SEQ ID NO 4
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4

```
aaaaaagctt cctgctcaga agaccggcgt ctcgcg                                  36
```

<210> SEQ ID NO 5
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5

```
aaaaaagctt cccaccatgg accaaatccc gatccgc                                 37
```

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6

```
tcagcgggcg ccgcgcgcgg cgac                                               24
```

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7

```
caccatgacc tggcttgagc cgcag                                              25
```

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 8
tcagcgggcg ccgcgcgcgg cgac                                          24
```

RECOMBINANT CELL PRODUCING 2-HYDROXYISOBUTYRIC ACID

CROSS-REFERENCE TO RELATED APPLICATIONS

The present application is a 35 U.S.C. § 371 National Stage patent application of International patent application PCT/EP09/055089, filed on Apr. 28, 2009, which claims priority to German patent application DE 102008002715.4, filed on Jun. 27, 2008.

FIELD OF THE INVENTION

The subject matter of the invention is a cell which has been genetically modified so as to be capable of producing more 2-hydroxyisobutyric acid or more polyhydroxyalkanoates containing 2-hydroxyisobutyric acid monomer units than its wild type, characterized in that 2-hydroxyisobutyric acid or polyhydroxyalkanoates containing 2-hydroxyisobutyric acid monomer units are produced via acetoacetyl-coenzyme A as intermediate and 3-hydroxybutyryl-coenzyme A as precursor.

PRIOR ART

Methacrylic acid, its esters and polymers are widely used for producing acrylic glass panes, injection-moulded products, coatings and many other products.

A plurality of processes for producing methacrylic acid have been described. However, most world-wide commercial production is based on a chemical process of hydrolysing methacrylamide sulphates produced from the corresponding 2-hydroxynitriles, with about 1.6 kg of sulphuric acid required for producing 1 kg of methacrylic acid.

U.S. Pat. No. 3,666,805 and U.S. Pat. No. 5,225,594 describe the chemical conversion of 2-hydroxyisobutyric acid (2-HIB) to methacrylic acid with yields of up to 96%.

An alternative process for producing methacrylic acid involves hydrolysing 2-hydroxynitriles to give 2-hydroxyisobutyric acid with utilization of nitrile-hydrolysing enzymes, the latter being nitrilase or a combination of nitrile hydratase and amidase (A. Banerjee, R. Sharrna, U. C. Banerjee, 2002, "The nitrile-degrading enzymes: current status and future prospects", Appl. Microbiol. Biotechnol., 60:33-44 and U.S. Pat. No. 6,582,943). A serious disadvantage of this method is the instability of nitriles in the neutral pH range which is needed for an efficient nitrile-hydrolysing enzyme activity. Nitrile degradation in the reaction mixture results in the accumulation of ketones and cyanide, both of which inhibit nitrile-hydrolysing enzyme activities.

A general disadvantage of both processes, i.e. of the currently dominating process based on amide sulphates and of the enzymatic nitrile-hydrolysing process, is the need for 2-hydroxynitriles which must first be prepared from environmentally harmful reactants, namely ketones and cyanide.

CA 2,510,657 discloses an alternative process for providing 2-hydroxyisobutyric acid via an enzymatic metabolic pathway by which tert-butyl alcohol is degraded.

PCT/EP2007/052830 discloses another enzymatic process for providing 2-hydroxyisobutyric acid. This involves converting the precursor 3-hydroxybutyryl-coenzyme A (3-HBCoA) to 2-hydroxyisobutyric acid with the aid of a mutase. In practice, said process has the following disadvantages: it is a batch process, the reactant 3-hydroxybutyric acid (3-HB) is added exogenously, and the process conditions demand inert gas. The rates of conversion are around 20%.

Processes for preparing 2-hydroxyisobutyric acid or polyhydroxyalkanoates containing 2-hydroxyisobutyric acid monomer units, which overcome the disadvantages described, would therefore be advantageous.

Consequently, it was the object of the invention to provide a process for producing 2-hydroxyisobutyric acid, which meets the demand for precursors for 2-hydroxyisobutyric acid or polyhydroxyalkanoates containing 2-hydroxyisobutyric acid monomer units, which can be processed further to give methacrylic acid, its esters and polymers.

DESCRIPTION OF THE INVENTION

Surprisingly, we found that producing 2-hydroxyisobutyric acid or polyhydroxyalkanoates containing 2-hydroxyisobutyric acid monomer units via acetoacetyl-coenzyme A as intermediate and 3-hydroxybutyryl-coenzyme A as precursor contributes to achieving the above-mentioned objects.

The term "precursor", as used herein, defines a chemical compound which can be converted enzymatically to the desired product by employing only one enzyme, while the term "intermediate" defines a chemical compound which can be converted enzymatically to the desired product by employing at least two enzymes; compounds with or without coenzyme A functionality should be regarded as equivalent "chemical compounds", and the thioester-forming or thioester-cleaving enzymes are therefore not included.

The invention therefore relates to a cell which has been genetically modified so as to be capable of producing more 2-hydroxyisobutyric acid or more polyhydroxyalkanoates containing 2-hydroxyisobutyric acid monomer units than its wild type, characterized in that 2-hydroxyisobutyric acid or polyhydroxyalkanoates containing 2-hydroxyisobutyric acid monomer units are produced via acetoacetyl-coenzyme A as intermediate and 3-hydroxybutyryl-coenzyme A as precursor. The invention further relates to a process for preparing the cell according to the invention and to a process for preparing 2-hydroxyisobutyric acid using a cell according to the invention and also to a process for preparing methacrylic acid.

One advantage of the invention is the possibility of preparing 2-hydroxyisobutyric acid and methacrylic acid, respectively, both from renewable resources, for example from carbohydrates and/or glycerol, but also from raw materials derived from fossil fuels, such as methanol for example, thereby avoiding the problems of varying availability of fossil resources.

Another advantage of the invention is the possibility of obtaining methacrylic acid in thermally less stressful and usually fewer steps of the process of the invention.

Yet another advantage of the invention consists in avoiding a multiplicity of toxic or aggressive substances as produced in conventional, chemical processes for preparing 2-hydroxyisobutyric acid.

The invention will be described by way of example hereinbelow but is not intended to be limited to these exemplary embodiments.

Unless indicated otherwise, all percentages (%) are given in percent by mass.

The term "2-hydroxyisobutyric acid", as used herein, always describes the corresponding $C_4$-carboxylic acid in the form present, depending on the pH, after being produced by the corresponding microorganisms. Consequently, said term always encompasses the pure acidic form (2-hydroxyisobutyric acid), the pure basic form (2-hydroxyisobutyrate) and mixtures of the protonated and deprotonated forms of the acid.

Furthermore, the term "3-hydroxybutyryl-coenzyme A" comprises in principle both the (R)-stereoisomer and the (S)-stereoisomer, with particular preference being given to the (R)-stereoisomer.

The phrase "so as to be capable of producing more 2-hydroxyisobutyric acid or more polyhydroxyalkanoates containing 2-hydroxyisobutyric acid monomer units than its wild type" also refers to the case in which the wild type of the genetically modified cell is not capable of producing any 2-hydroxyisobutyric acid or any polyhydroxyalkanoates containing 2-hydroxyisobutyric acid monomer units at all or at least any detectable quantities of these compounds, and detectable amounts of these components can be produced only after the genetic modification.

A "wild type" preferably refers to a cell whose genome has been generated naturally by evolution. The term is used both for the cell as a whole and for individual genes. Consequently, the term "wild type" specifically does not include those cells and genes whose gene sequences have been modified at least partially by humans by means of recombinant processes.

Methacrylic acid may then be produced from 2-hydroxyisobutyric acid in a gentle dehydration reaction. In the case of polyhydroxyalkanoates containing 2-hydroxyisobutyric acid monomer units, the grana present in the cells, which are charged with said polyhydroxyalkanoates, may be isolated, and subsequently the polymers may be cleaved to give 2-hydroxyisobutyric acid which may then be dehydrated to give methacrylic acid.

According to the invention, preference is given here to the genetically modified cell having been genetically modified so as to produce at least two times, particularly preferably at least ten times, additionally preferably at least 100 times, additionally still more preferably at least 1000 times and most preferably at least 10 000 times, more 2-hydroxyisobutyric acid or polyhydroxyalkanoates containing 2-hydroxyisobutyric acid monomer units than the wild-type cell within a defined time interval, preferably within 2 hours, still more preferably within 8 hours and most preferably within 24 hours. The increase in product formation may be determined, for example, by culturing the cell according to the invention and the wild-type cell in each case separately under the same conditions (same cell density, same nutrient medium, same culturing conditions) in a suitable nutrient medium for a particular time interval and then determining the amount of target product (2-hydroxyisobutyric acid or polyhydroxyalkanoates containing 2-hydroxyisobutyric acid monomer units), either, in the case of 2-hydroxyisobutyric acid, in the cell supernatant or, in the case of polyhydroxyalkanoates containing 2-hydroxyisobutyric acid monomer units, in the cells.

The cells of the invention may be prokaryotes or eukaryotes and may be mammalian cells (such as human cells), plant cells or microorganisms such as yeasts, fungi or bacteria, with particular preference being given to microorganisms and most preference being given to bacteria and yeasts.

Suitable bacteria, yeasts or fungi are in particular those bacteria, yeasts or fungi deposited with the Deutsche Sammlung von Mikroorganismen and Zellkulturen GmbH (DSMZ) [German collection of microorganisms and cell cultures], Brunswick, Germany, in the form of bacterial, yeast or fungal strains. Bacteria suitable according to the invention belong to the genera listed at
http://www.dsmz.de/species/bacteria.htm,
yeasts suitable according to the invention belong to those genera listed at
http://www.dsmz.de/species/yeasts.htm
and fungi suitable according to the invention are those listed at
http://www.dsmz.de/species/fungi.htm.

Preferred cells of the invention are those of the genera *Aspergillus, Corynebacterium, Brevibacterium, Bacillus, Acinetobacter, Alcaligenes, Lactobacillus, Paracoccus, Lactococcus, Candida, Pichia, Hansenula, Kluyveromyces, Saccharomyces, Escherichia, Zymomonas, Yarrowia, Methylobacterium, Ralstonia, Pseudomonas, Rhodospirillum, Rhodobacter, Burkholderia, Clostridium* and *Cupriavidus*, with particular preference being given to *Aspergillus nidulans, Aspergillus niger, Alcaligenes latus, Bacillus megaterium, Bacillus subtilis, Brevibacterium flavum, Brevibacterium lactofermentum, Escherichia coli, Saccharomyces cerevisiae, Kluveromyces lactis, Candida blankii, Candida rugosa, Corynebacterium glutamicum, Corynebacterium efficiens, Zymomonas mobilis, Yarrowia lipolytica, Hansenula polymorpha, Methylobacterium extorquens, Ralstonia eutropha*, in particular *Ralstonia eutropha* H16, *Rhodospirillum rubrum, Rhodobacter sphaeroides, Paracoccus versutus, Pseudomonas aeruginosa, Pseudomonas putida, Acinetobacter calcoaceticus* and *Pichia pastoris*.

The cell according to the invention which is capable of producing more 2-hydroxyisobutyric acid or more polyhydroxyalkanoates containing 2-hydroxyisobutyric acid monomer units than its wild type via acetoacetyl-coenzyme A as intermediate and 3-hydroxybutyryl-coenzyme A as precursor therefore has an activity of an enzyme $E_1$ catalysing the conversion from acetoacetyl-coenzyme A to 3-hydroxybutyryl-coenzyme A.

The enzyme $E_1$ is preferably an enzyme selected from the group comprising:
a 3-hydroxyacyl-CoA dehydrogenase (EC 1.1.1.35),
an acetoacetyl-coenzyme A reductase (EC 1.1.1.36),
a long-chain 3-hydroxyacyl-CoA dehydrogenase ((EC 1.1.1.211) and
a 3-hydroxybutyryl-coenzyme A dehydrogenase (EC 1.1.1.157).

Said enzyme is preferably encoded by the genes selected from the group consisting of phaB, phbB, fabG, phbN1, phbB2, particularly preferably phaB, phbB. The nucleotide sequences of said genes can be found, for example, in the "Kyoto Encyclopedia of Genes and Genomes" (KEGG database), the databases of the National Center for Biotechnology Information (NCBI) of the National Library of Medicine (Bethesda, Md., USA) or the nucleotide sequence database of the European Molecular Biologies Laboratories (EMBL, Heidelberg, Germany and Cambridge, UK).

It may be advantageous for the cell according to the invention to have an increased enzyme $E_1$ activity compared to its wild type, which enzyme catalyses the conversion of acetoacetyl-coenzyme A to 3-hydroxybutyryl-coenzyme A.

The term "increased enzyme activity", as used above in connection with enzyme $E_1$ and in the comments hereinbelow in connection with enzymes $E_2$ etc., preferably means an increased intracellular activity.

The following comments on increasing the enzyme activity in cells apply to both the increase in activity of enzyme $E_1$ and to all other enzymes mentioned hereinbelow whose activity may be increased, where appropriate.

An increase in enzymatic activity can be achieved in principle by increasing the copy number of the gene sequence or gene sequences coding for the enzyme, by using a strong promoter, by altering the codon usage of the gene, by increasing the half life of the mRNA or the enzyme in different ways, by modifying the regulation of expression of the gene or by utilizing a gene or allele coding for a corresponding enzyme having increased activity and by combining these measures, where appropriate. Genetically modified cells of the invention are generated, for example, by transformation, transduction, conjugation or a combination of these methods, using a vector which contains the desired gene, an allele of said gene or parts thereof and a promoter enabling the gene to be expressed. Heterologous expression is achieved in particular by integrating the gene or the alleles in the chromosome of the cell or in an extrachromosomally replicating vector.

An overview of the possibilities of increasing the activity of enzymes in cells is given, for the example of pyruvate carboxylase, in DE-A-100 31 999 which is hereby incorporated by reference and whose disclosure on the possibilities of increasing the activity of enzymes in cells is part of the disclosure of the present invention.

Expression of the enzymes or genes mentioned above and of all enzymes or genes mentioned hereinbelow may be detected with the aid of one- and two-dimensional protein gel fractionation and subsequent optical identification of protein concentration in the gel by appropriate evaluation software. If the increase in an enzyme activity is based only on an increase in expression of the corresponding gene, said increase in enzyme activity may be quantified simply by comparing the one- or two-dimensional protein fractionations of wild type and genetically modified cell. A customary method of preparing protein gels for coryneform bacteria and identifying said proteins is the procedure described by Hermann et al. (Electrophoresis, 22: 1712.23 (2001)). Protein concentration may likewise be analysed by Western blot hybridization with an antibody specific to the protein to be detected (Sambrook et al., Molecular Cloning: a laboratory manual, 2nd Ed. Cold Spring Harbor Laboratory Press, Cold Spring Harbor, N.Y. USA, 1989) and subsequent optical evaluation using appropriate concentration determination software (Lohaus and Meyer (1989) Biospektrum, 5: 32-39; Lottspeich (1999), Angewandte Chemie 111: 2630-2647). The activity of DNA-binding proteins may be measured by means of DNA-band shift assays (also referred to as gel retardation) (Wilson et al. (2001) Journal of Bacteriology, 183: 2151-2155). The action of DNA-binding proteins on the expression of other genes may be detected by various well-described reporter gene assay methods (Sambrook et al., Molecular Cloning: a laboratory manual, 2nd Ed. Cold Spring Harbor Laboratory Press, Cold Spring Harbor, N.Y. USA, 1989). Intracellular enzymatic activities may be determined by various described methods (Donahue et al. (2000) Journal of Bacteriology 182 (19): 5624-5627; Ray et al. (2000) Journal of Bacteriology 182 (8): 2277-2284; Freedberg et al. (1973) Journal of Bacteriology 115 (3): 816-823). Where the comments hereinbelow do not indicate any specific methods of determining the activity of a particular enzyme, the increase in enzyme activity and also the reduction of an enzyme activity are preferably determined by the methods described in Hermann et al., Electrophoresis, 22: 1712-23 (2001), Lohaus et al., Biospektrum 5 32-39 (1998), Lottspeich, Angewandte Chemie 111: 2630-2647 (1999) and Wilson et al., Journal of Bacteriology 183: 2151-2155 (2001).

If the increase in enzyme activity is accomplished by mutating the endogenous gene, such mutations may be generated either unspecifically by classical methods, for example by UV irradiation or mutagenic chemicals, or specifically by means of genetic engineering methods such as deletion(s), insertion(s) and/or nucleotide substitution(s). Said mutations produce altered cells. Particularly preferred mutant enzymes are in particular also those enzymes which cannot be inhibited by feedback anymore or only to a limited extent compared with the wild-type enzyme.

Where the increase in enzyme activity is accomplished by increasing enzyme synthesis, this involves for example increasing the copy number of the corresponding genes or mutating the promoter and regulatory regions or the ribosomal binding site located upstream of the structural gene. Expression cassettes inserted upstream of the structural gene have the same effect. In addition, inducible promoters enable expression to be increased at any time. Furthermore, however, "enhancers" which also increase gene expression by way of increased interaction between RNA polymerase and DNA may also be assigned as regulatory sequences to the enzyme gene. Measures of prolonging the life time of mRNA also improve expression. Furthermore, enzyme activity is also enhanced by preventing degradation of the enzyme protein. Here, the genes or gene constructs are either located in plasmids with different copy numbers or integrated and amplified in the chromosome. Alternatively, the genes in question may furthermore be overexpressed by altering media compositions and culturing procedures. Instructions for this can be found by the skilled worker inter alia in Martin et al. (Bio/Technology 5, 137-146 (1987)), in Guerrero et al. (Gene 138, 35-41 (1994)), Tsuchiya and Morinaga (Bio/Technology 6, 428-430 (1988)), in Eikmanns et al. (Gene 102, 93-98 (1991)), in EP-A-0 472 869, in U.S. Pat. No. 4,601,893, in Schwarzer and Puhler (Bio/Technology 9, 84-87 (1991)), in Reinscheid et al. (Applied and Environmental Microbiology 60, 126-132 (1994)), in LaBarre et al. (Journal of Bacteriology 175, 1001-1007 (1993)), in WO-A-96/15246, in Malumbres et al. (Gene 134, 15-24 (1993), in JP-A-10-229891, in Jensen and Hammer (Biotechnology and Bioengineering 58, 191-195 (1998)) and in known genetics and molecular biology textbooks. Like the mutations, the measures described above result in genetically modified cells. Expression of the particular genes is increased by employing episomal plasmids, for example. Suitable plasmids and vectors are in principle all embodiments available to the skilled worker for this purpose. Such plasmids and vectors may be found, for example, in brochures from Novagen, Promega, New England Biolabs, Clontech or Gibco BRL. Other preferred plasmids and vectors may be found in: Glover, D. M. (1985), DNA cloning: a practical approach, vol. I-III, IRL Press Ltd., Oxford; Rodriguez, R. L. and Denhardt, D. T (eds) (1988), Vectors: a survey of molecular cloning vectors and their uses, 179-204, Butterworth, Stoneham; Goeddel, D. V. (1990), Systems for heterologous gene expression, Methods Enzymol. 185, 3-7; Sambrook, J.; Fritsch, E. F. and Maniatis, T. (1989), Molecular cloning: a laboratory manual, 2nd ed., Cold Spring Harbor Laboratory Press, New York.

The plasmid vector containing the gene to be amplified is then transferred by conjugation or transformation to the desired strain. The method of conjugation is described, for example, in Schäfer et al., Applied and Environmental Microbiology 60: 756-759 (1994). Methods of transformation are described, for example, in Thierbach et al., Applied Microbiology and Biotechnology 29: 356-362 (1988), Dunican and Shivnan, Bio/Technology 7: 1067-1070 (1989) and Tauch et al., FEMS Microbiology Letters 123: 343-347 (1994). After homologous recombination by means of a cross-over event, the resultant strain contains at least two copies of the gene in question. The phrase "a higher enzyme $E_x$ activity than its wild type" used above and in the comments below always means preferably an activity of the particular enzyme $E_x$, which has increased by a factor of at least 2, particularly preferably of at least 10, additionally preferably of at least 100, additionally still more preferably of at least 1000 and most preferably of at least 10 000. The cell according to the invention having "a higher enzyme $E_x$ activity than its wild type", furthermore comprises more specifically also a cell whose wild type has no or at least no detectable activity of said enzyme $E_x$ and which exhibits a detectable activity of said enzyme $E_x$ only after said enzyme activity has been increased, for example by overexpression. In this context, the term "overexpression" or the phrase "increase in expression" used in the comments hereinbelow also comprises the case in which a starting cell, for example a wild-type cell, has no or at least no detectable expression and detectable synthesis of enzyme $E_x$ is induced only by recombinant processes. Accordingly, the phrase "lower enzyme $E_x$ activity" used hereinbelow preferably means an activity which has been reduced by a factor of at least 0.5, particularly preferably of at least 0.1, additionally preferably of at least 0.01, additionally still more preferably of at least 0.001 and most preferably of at least 0.0001. The phrase "lower activity" also includes no detectable activity ("zero activity"). The activity of a particular enzyme may be reduced, for example, by specific mutation, by adding competitive or non-competitive inhibitors or by other measures of reducing the activity of a particular enzyme which are known to the skilled worker.

Preferably, the cell according to the invention that is capable of producing more 2-hydroxyisobutyric acid or more polyhydroxyalkanoates containing 2-hydroxyisobutyric acid monomer units via acetoacetyl-coenzyme A as intermediate and 3-hydroxybutyryl-coenzyme A as precursor than its wild type can utilize carbohydrates, glycerol, oils and fats, carbon dioxide, carboxylic acids or methanol as carbon source.

Furthermore, the cell according to the invention that is capable of producing 2-hydroxyisobutyric acid or polyhydroxyalkanoates containing 2-hydroxyisobutyric acid monomer units via acetoacetyl-coenzyme A as intermediate and 3-hydroxybutyryl-coenzyme A as precursor preferably has, where appropriate in addition to the activity of enzyme $E_1$, an activity of an enzyme $E_2$, which is preferably higher than that of its wild type and which catalyses the conversion of two acetyl-coenzyme A molecules to acetoacetyl-coenzyme A.

The enzyme $E_2$ is preferably an acetyl-CoA C-acetyltransferase (EC 2.3.1.9). This enzyme is preferably encoded by the genes selected from the group consisting of acat1, acat2, loc484063, loc489421, mgc69098, mgc81403, mgc81256, mgc83664, kat-1, erg10, ygeF, atoB, fadAx, phbA-1, phbA-2, atoB-2, pcaF, pcaF-2, phb-A, bktB, phaA, tioL, thlA, fadA, paaJ, phbAf, pimB, mmgA, yhfS, thl, vraB, th1, mvaC, thiL, paaJ, fadA3, fadA4, fadA5, fadA6, cg112392, catF, sc8f4.03, thiL1, thiL2, acaB1, acaB2, acaB3 or acaB4, with particular preference being given to acat1, acat2, atoB, thlA, thlB, phaA and phbA, particularly preferably phaA and phbA.

The nucleotide sequences of these genes can be found, for example, in the "Kyoto Encyclopedia of Genes and Genomes" (KEGG database), the databases of the National Center for Biotechnology Information (NCBI) of the National Library of Medicine (Bethesda, Md., USA) or in the nucleotide sequence database of the European Molecular Biologies Laboratories (EMBL, Heidelberg, Germany and Cambridge, UK).

The cell according to the invention has preferably at least one activity of an enzyme $E_3$, which is preferably higher than that of its wild type and which catalyses the conversion of 3-hydroxybutyryl-coenzyme A to 2-hydroxyisobutyryl-coenzyme A. The enzyme $E_3$ is preferably a hydroxyisobutyryl-CoA mutase, an isobutyryl-CoA mutase (EC 5.4.99.13) or a methylmalonyl-CoA mutase (EC 5.4.99.2), in each case preferably a coenzyme B12-dependent mutase.

The enzyme $E_3$ can be isolated preferably from the microorganisms *Aquincola tertiaricarbonis* L108, DSM18028, DSM18512, *Methylibium petroleiphilum* PM1, *Methylibium* sp. R8, *Xanthobacter autotrophicus* Py2, *Rhodobacter sphaeroides* (ATCC 17029), *Nocardioides* sp. JS614, *Marinobacter algicola* DG893, *Sinorhizobium medicae* WSM419, *Roseovarius* sp. 217, *Pyrococcus furiosus* DSM 3638 and is particularly preferably the coenzyme B12-dependent mutase described in PCT/EP2007/052830, and is also one of those enzymes whose sequences are in at least one part at least 60%, preferably at least 80%, particularly preferably at least 95%, very particularly preferably at least 99%, identical at the amino acid level to the amino acid sequence of the small or the large subunit of the mutase described in PCT/EP2007/052830 (accession number DQ436457.1 and DQ436456.1), as determined by the blastp algorithm with an expect threshold of 10, a word size of 3, a blosum62 matrix with gap costs of existence: 11 and extension: 1 and a conditional compositional score matrix adjustment.

In a preferred embodiment of the cell according to the invention capable of producing 2-hydroxyisobutyric acid or polyhydroxyalkanoates containing 2-hydroxyisobutyric acid monomer units via acetoacetyl-coenzyme A as intermediate and 3-hydroxybutyryl-coenzyme A as precursor, the cell according to the invention in its wild-type form has an activity of an enzyme $E_4$, preferably a lower activity of at least one enzyme $E_4$ than its wild type, which enzyme catalyses the conversion of 3-hydroxybutyryl-coenzyme A to polyhydroxybutyrate.

The enzyme $E_4$ is preferably a polyhydroxyalkanoate synthase, particularly preferably a polyhydroxybutyrate synthase. This enzyme is preferably encoded by the genes phbC and phaC, with particular preference being given to phaC.

In a further, preferred embodiment of the cell according to the invention capable of producing 2-hydroxyisobutyric acid or polyhydroxyalkanoates containing 2-hydroxyisobutyric acid monomer units via acetoacetyl-coenzyme A as intermediate and 3-hydroxybutyryl-coenzyme A as precursor, the cell according to the invention in its wild-type form has an activity of an enzyme $E_5$, preferably a lower activity of an enzyme $E_5$ than its wild type, which enzyme catalyses the conversion of 3-hydroxybutyryl-coenzyme A to crotonyl-coenzyme A.

The enzyme $E_5$ is preferably a crotonase (EC 4.2.1.55) or a (3R)-3-hydroxybutanoyl-CoA dehydratase (EC 4.2.1.17). This enzyme is preferably encoded by the genes selected from the group consisting of crt, crt1, crt2, fadB, paaF, with preference being given to crt and the corresponding gene from clostridia and particular preference being given to *Clostridium acetobutylicum* crt.

In yet another, preferred embodiment of the cell according to the invention capable of producing 2-hydroxyisobutyric acid or polyhydroxyalkanoates containing 2-hydroxyisobutyric acid monomer units via acetoacetyl-coenzyme A as intermediate and 3-hydroxybutyryl-coenzyme A as precursor, the cell according to the invention has an activity of an enzyme $E_6$, preferably a lower activity of an enzyme $E_6$ than its wild type, which enzyme catalyses the conversion of R-3-hydroxybutyryl-coenzyme A to S-3-hydroxybutyryl-coenzyme A.

The enzyme $E_6$ is preferably a 3-hydroxybutyryl-CoA epimerase (EC 5.1.2.3). This enzyme is preferably encoded by the genes selected from the group consisting of fadB, fadB1, fadB2, fadJ, fabJ-1, faoA, yfcX, with preference being given to fadB, fadJ, yfcX and particular preference being given to fadB, fadJ.

Furthermore, the cell according to the invention capable of producing 2-hydroxyisobutyric acid or polyhydroxyalkanoates containing 2-hydroxyisobutyric acid monomer units via acetoacetyl-coenzyme A as intermediate and 3-hydroxybutyryl-coenzyme A as precursor preferably has a lower activity of at least one enzyme $E_7$ than its wild type, which enzyme accepts 3-hydroxybutyryl-coenzyme A as substrate.

Another contribution to achieving the objects stated at the outset is made by a process for preparing 2-hydroxyisobutyric acid or polyhydroxyalkanoates containing 2-hydroxyisobutyric acid monomer units, comprising the steps of:
a) contacting a cell according to the invention with a nutrient medium including a carbon source under conditions where 2-hydroxyisobutyric acid or polyhydroxyalkanoates containing 2-hydroxyisobutyric acid monomer units are produced from the carbon source, and where appropriate,
b) purifying the 2-hydroxyisobutyric acid from the nutrient medium or polyhydroxyalkanoates containing 2-hydroxyisobutyric acid monomer units from the cells.

Examples of carbon sources which may be used are carbohydrates [such as, for example, monosaccharides (e.g. glucose, fructose, galactose, arabinose, xylose), oligosaccharides (e.g. maltose, saccharose, lactose), and polysacharides (e.g. starch, hydrolysed starch, cellulose, hydrolysed cellulose, hemicellulose, hydrolysed hemicellulose)], and reaction products thereof such as, for example, sugar alcohols and polyhydroxy acids; carbon dioxide;
organic mono-, di- and tricarboxylic acids optionally carrying 1 or more, e.g. 1, 2, 3 or 4, hydroxyl groups, e.g. acetic acid, tartaric acid, itaconic acid, succinic acid, propionic acid, lactic acid, 3-hydroxypropionic acid, fumaric acid, maleic acid, 2,5-furandicarboxylic acid, glutaric acid, laevulinic acid, gluconic acid, aconitic acid, succinic acid and diaminopimelic acid, citric acid;
lipids;
oils or fats such as, for example, rapeseed oil, soya oil, palm oil, sunflower oil, groundnut oil and coconut oil;
saturated and unsaturated fatty acids, preferably with from 10 to 22 carbons, for example γ-linolenic acid, dihomo-γ-linolenic acid, arachidonic acid, palmitic acid, stearic acid, linoleic acid, eicosapentaenoic acid and docosahexaenoic acid; hydrocarbons such as methane;
alcohols, for example with from 1 to 22 carbons, e.g. butanol, methanol, ethanol;
diols, preferably with from 3 to 8 carbons, e.g. propanediol and butanediol;
polyhydric (also referred to as higher) alcohols with 3 or more, for example 3, 4, 5 or 6, OH groups, e.g. glycerol, sorbitol, mannitol, xylitol and arabinitol;
ketones, preferably with from 3 to 10 carbons and, where appropriate, 1 or more hydroxyl groups, e.g. acetone and acetoin;
lactones, e.g. γ-butyrolactone, cyclodextrins, biopolymers, e.g. polyhydroxyacetate, polyesters, e.g. polylactide, polysaccharides, polyisoprenoids, polyamides;
aromatic compounds, e.g. aromatic amines, vanillin and indigo; proteins, for example enzymes such as amylases, pectinases, acidic, hybrid or neutral cellulases, esterases such as lipases, pancreases, proteases, xylanases and oxidoreductases such as laccase, catalase and peroxidase, glucanases, phytases; carotenoids, e.g. lycopene, β-carotene, astaxanthin, zeaxanthin and canthaxanthin;
proteinogenic and non-proteinogenic amino acids, e.g. lysine, glutamate, methionine, phenylalanine, aspartic acid, tryptophan and threonine;
purine and pyrimidine bases;
nucleosides and nucleotides, e.g. nicotinamide-adenine dinucleotide (NAD) and adenosine 5'-monophosphate (AMP);
and also precursors and derivatives, for example salts of the acids mentioned, of the compounds mentioned above.

These substances may be used individually or as mixture. Particular preference is given to using carbohydrates, in particular monosaccharides, oligosaccharides or polysaccharides, as described in U.S. Pat. No. 6,136,576 for example, $C_5$ sugars or glycerol. A preferred alcohol to be used is methanol, since it can be prepared from many different sources such as, for example, biogas, biomass, natural gas or coal.

The carbon sources may be used in different forms (pure or in solution/suspension) and in different compositions (purified or as crude product) from different processing stages (e.g. sugar-cane juice, syrup, molasses, unrefined sugar, refined sugar crystals; grain of maize, flour, starch, dextrin, glucose), before or after treatment (steam explosion, pre-treatment with acid, pre-treatment with enzyme).

In a preferred, alternative embodiment, the carbon source comprises $CO_2$ or CO, in particular syngas. The cells according to the invention used in this connection are acetogenic cells such as, for example, species of the genus *Acetobacterium*, such as *A. woodii* and *Clostridium aceticum*. More specifically, said acetogenic cells are selected from the group comprising *Thermoanaerobacter kivui*, *Acetobacterium woodii*, *Acetoanaerobium notera*, *Clostridium aceticum*, *Butyribacterium methylotrophicum*, *Clostridium acetobutylicum*, *Moorella thermoacetica*, *Eubacterium limosum*, *Peptostreptococcus productus*, *Clostridium ljungdahlii* and *Clostridium carboxidivorans*. A particularly suitable cell in this connection is *Clostridium carboxidivorans*, in particular strains such as "p7" and "p11". Such cells are described in US 2007/0275447 and US 2008/0057554, for example. Another cell which is particularly suitable in this connection is *Clostridium ljungdahlii*, in particular strains selected from the group comprising *Clostridium ljungdahlii* PETC, *Clostridium ljungdahlii* ERI2, *Clostridium ljungdahlii* C01 and *Clostridium ljungdahlii* O-52, as described in WO 98/00558 and WO 00/68407.

The genetically modified cells according to the invention may be contacted with the nutrient medium and thus cultured in a continuous process or in a batch process (batch culture) or in the fed-batch process or repeated fed-batch process for the purpose of producing 2-hydroxyisobutyrate or polyhydroxyalkanoates containing 2-hydroxyisobutyric acid monomer units. A semi-continuous process, as described in GB-A-1009370 for example, is also conceivable. A review of other known culturing methods is described in the textbook by Chmiel ("*Bioprozesstechnik 1. Einführung in die Bioverfahrenstechnik*" [Bioprocessing 1. Introduction to bioprocessing] (Gustav Fischer Verlag, Stuttgart, Germany, 1991)) or in the textbook by Storhas ("*Bioreaktoren and periphere Einrichtungen*" [Bioreactors and peripheral equipment], Vieweg Verlag, Brunswick/Wiesbaden, Germany, 1994).

The culture medium to be used must be suited to the requirements of the particular strains. Culture media for various microorganisms are described in the "*Manual of Methods for General Bacteriology*" of the American Society for Bacteriology (Washington D.C., USA, 1981).

Nitrogen sources which may be used are organic compounds containing nitrogen, such as peptones, yeast extract, meat extract, malt extract, corn steep liquor, soya meal and urea or inorganic compounds such as ammonium sulphate, ammonium chloride, ammonium phosphate, ammonium carbonate and ammonium nitrate. The nitrogen sources may be used individually or as mixture.

Phosphorus sources which may be used are phosphoric acid, potassium dihydrogen phosphate or dipotassium hydrogen phosphate or the corresponding sodium salts. The culture medium should furthermore contain metal salts such as, for example, magnesium sulphate or iron sulphate, which are required for growth. Finally, essential growth substances such as amino acids and vitamins may be used in addition to the substances mentioned above. What is more, suitable precursors may be added to the culture medium. Said substances for use may be introduced to the culture in a single addition or fed in a suitable manner during culturing.

The pH of the culture is controlled by using basic compounds such as sodium hydroxide, potassium hydroxide, ammonia or aqueous ammonia, or acidic compounds such as phosphoric acid or sulphuric acid in a suitable manner. Foaming can be controlled by using antifoams such as fatty acid polyglycol esters, for example. Plasmid stability can be maintained by adding to the medium suitable selective agents such as antibiotics, for example. Aerobic conditions are maintained by introducing into the culture oxygen or oxygen-containing gas mixtures such as air, for example. The culture temperature is usually from 20° C. to 45° C. and preferably from 25° C. to 40° C. Preference may be given to using cells such as those described in U.S. Pat. No. 6,803,218, in particular if said cells are capable of converting glycerol as substrate. In this case the cells may be cultured at temperatures ranging from 40 to 100° C.

The purification of 2-hydroxyisobutyric acid from the nutrient solution is preferably carried out continuously, it being furthermore preferred in this context also to produce 2-hydroxyisobutyric acid by fermentation in a continuous manner, so that the entire process from production of 2-hydroxyisobutyric acid up to its purification from the fermentation broth can be carried out continuously. For continuous purification of the preparation of 2-hydroxyisobutyric acid from the fermentation broth, the latter is continuously passed through a device for removing the microorganisms employed during fermentation, preferably through a filter with a cut-off in the range from 20 to 200 kDa, where solid/liquid separation takes place. It is also feasible to employ a centrifuge, a suitable sedimentation device or a combination of these devices, it being especially preferred to first separate at least part of the microorganisms by sedimentation and subsequently to feed the fermentation broth, which has been partly relieved of the microorganisms, to ultrafiltration or to a centrifugation device.

After the microorganisms have been removed, the fermentation product which is enriched with regard to its 2-hydroxyisobutyric acid content, is fed to a separation system, preferably a multistep separation system. This separation system provides for a plurality of separation steps which are connected in series, from which steps in each case return lines lead away and back to the fermentation tank. Furthermore, exit pipes lead out of the respective separation steps. The individual separation steps may operate by the electrodialysis, the reverse osmosis, the ultrafiltration or the nanofiltration principle. As a rule, the individual separation steps comprise membrane separation devices. The individual separation steps are selected due to the nature and the extent of the fermentation by-products and residual substrates.

Besides being removed by means of electrodialysis, reverse osmosis, ultrafiltration or nanofiltration, where the end product obtained is an aqueous 2-hydroxyisobutyric acid solution, 2-hydroxyisobutyric acid may also be removed by extractive methods from the fermentation solution which has been relieved of microorganisms, in which case pure 2-hydroxyisobutyric acid may ultimately be obtained. 2-Hydroxyisobutryic acid may be removed by extraction by adding to the fermentation solution, for example, ammonium compounds or amines to produce an ammonium salt of 2-hydroxyisobutyric acid. This ammonium salt can then be removed from the fermentation solution by adding an organic extractant and subsequently heating the resulting mixture, whereby the ammonium salt is concentrated in the organic phase. 2-Hydroxyisobutyric acid can then be isolated from this phase, for example, by further extraction steps, to give pure 2-hydroxyisobutyric acid. More details regarding this separation method can be found in WO-A-02/090312, whose disclosure regarding the separation of hydroxycarboxylic acids from fermentation solutions is hereby incorporated by reference and forms part of the disclosure of the present application.

Depending on the way in which 2-hydroxyisobutyric acid is removed from the fermentation solution, either an aqueous solution of 2-hydroxyisobutyric acid comprising from 2 to 90% by weight, preferably 7.5 to 50% by weight and particularly preferably 10 to 25% by weight, of 2-hydroxyisobutyric acid, or else pure 2-hydroxyisobutyric acid is obtained.

With increasing concentrations 2-hydroxyisobutyric acid tends to form its cyclic dimer (tetramethylglycolide, TMG). This dimer can be treated similarly to 2-hydroxyisobutyric acid in the dehydration step of the process according to the invention and will therefore for this process step always be included in the term "2-hydroxyisobutyric acid" hereinbelow.

Furthermore, the 2-hydroxyisobutyric acid prepared by the process according to the invention may also be neutralized before, during or after purification, for which purpose for example bases such as alkali metal or alkaline earth metal hydroxides, e.g. calcium hydroxide or sodium hydroxide or else $NH_3$ or $NH_4OH$ for example, can be employed.

A contribution to achieving the objects stated at the outset is made in particular also by a process for preparing methacrylic acid or methacrylic esters, comprising the steps of:

IA) preparing 2-hydroxyisobutyric acid by the process described above and, where appropriate, purifying and/or neutralizing the 2-hydroxyisobutyric acid, IB) dehydrating the 2-hydroxyisobutyric acid with production of methacrylic acid and, where appropriate, esterifying the methacrylate or methacrylic acid.

According to step IB), 2-hydroxyisobutyric acid is dehydrated with formation of methacrylic acid, for which reaction it is possible either to use the pure 2-hydroxyisobutyric acid isolated from the fermentation solution or else the aqueous solution of 2-hydroxyisobutryic acid, which has been isolated during work-up of the fermentation solution and, where appropriate, is also concentrated, for example by means of distillation, where appropriate in the presence of a suitable entrainer, prior to the dehydration step.

The dehydration step may be performed in principle in the liquid phase or in the gas phase. Furthermore, preference is given in accordance with the invention to performing the dehydration step in the presence of a catalyst, the type of which depends on whether the reaction is carried out in the gas phase or in the liquid phase.

Suitable dehydration catalysts are both acidic and alkaline catalysts. Acidic catalysts are preferred, in particular because of their low tendency to form oligomers. The dehydration catalyst may be employed both as a homogeneous and as a heterogeneous catalyst. If the dehydration catalyst is a heterogeneous catalyst, preference is given to the dehydration catalyst being in contact with a support x. Appropriate supports x are all solids considered suitable by the skilled worker. In this context, preference is given to said solids having suitable pore volumes which are well suited to binding and absorbing the dehydration catalyst. In addition, preference is given to total pore volumes, as specified by DIN 66133, ranging from 0.01 to 3 ml/g, with particular preference being given to total pore volumes ranging from 0.1 to 1.5 ml/g. Moreover, the solids suitable as support x preferably have a surface area in the range from 0.001 to 1000 $m^2/g$, preferably in the range from 0.005 to 450 $m^2/g$ and additionally preferably in the range from 0.01 to 300 $m^2/g$, as determined by a BET test according to DIN 66131. A first support which may be employed for the dehydration catalyst is bulk material with a mean particle diameter in the range from 0.1 to 40 mm, preferably in the range from 1 to 10 mm, and additionally preferably in the range from 1.5 to 5 mm. The wall of the dehydration reactor may also serve as support.

Furthermore, the support may be acidic or basic per se, or else an acidic or basic dehydration catalyst may be applied to an inert support. Application techniques which may be mentioned in particular are immersion or impregnation or incorporation into a support matrix.

Suitable supports x, which may also feature dehydration catalyst properties, are, in particular, natural or synthetic silicates such as, in particular, mordenite, montmorillonite, acidic zeolites; supports which are coated with monobasic, dibasic or polybasic inorganic acids, in particular phosphoric acid, or with acidic salts of inorganic acids, such as substances of the oxide or silicate type, for example $Al_2O_3$, $TiO_2$; oxides and mixed oxides such as, for example, $\gamma$-$Al_2O_3$ and ZnO—$Al_2O_3$ mixed oxides of the heteropolyacids.

In accordance with an embodiment according to the invention, the support x consists at least in part of a compound of the oxide type. Such compounds of the oxide type should feature at least one of the elements selected from among Si, Ti, Zr, Al, P or a combination of at least two of these. Such supports may also act as dehydration catalyst themselves, owing to their acidic or basic properties. A preferred class of compounds acting both as support by way of x and as dehydration catalyst comprise silicon/aluminium/phosphorus oxides. Preferred basic substances which act both as dehydration catalyst and as support x comprise alkali metals, alkaline earth metals, lanthanum, lanthanoids or a combination of at least two of these in the form of their oxides. Such acidic or basic dehydration catalysts are commercially available both from Evonik Degussa GmbH and from Südchemie AG. A further class are ion exchangers which may also be basic or acidic.

Suitable homogeneous dehydration catalysts are, in particular, inorganic acids, preferably phosphorus-containing acids and additionally preferably phosphoric acid. These inorganic acids can be immobilized on the support x by immersion or impregnation.

The use of heterogeneous catalysts has proved particularly advantageous in particular in the case of gas phase dehydration. In the case of liquid-phase dehydration, however, both homogeneous and heterogeneous dehydration catalysts are employed.

Moreover, preference is given to the process according to the invention involving the use of a dehydration catalyst with an HO value in the range from +1 to −10, preferably in the range from +2 to −8.2 and additionally preferably, with liquid-phase dehydration, in the range from +2 to −3 and in gas-phase dehydration in the range from −3 to −8.2. The HO value corresponds to the acid function as defined by Hämmert and can be determined by what is known as amine titration and the use of indicators, or by absorption of a gaseous base (see "Studies in Surface Science and Catalytics", vol. 51, 1989: "New solid Acids and Bases, their catalytic Properties", K. Tannabe et al).

According to a particular embodiment of the process according to the invention, the acidic solid catalyst employed is a porous support structure which has been brought into contact with an inorganic acid, preferably with phosphoric acid or with superacids such as, for example, sulphated or phosphated zirconium oxide and which is based preferably to an extent of at least 90% by weight, additionally preferably at least 95% by weight and most preferably at least 99% by weight on a silicon oxide, preferably $SiO_2$. The porous support structure is brought into contact with the inorganic acid preferably by impregnating said support structure with said acid, with the amount of the latter being preferably in a range from 10 to 70% by weight, particularly preferably in a range from 20 to 60% by weight and additionally preferably in a range from 30 to 50% by weight, based on the weight of the support structure, followed by drying of the acid. After drying, the inorganic acid is fixed by heating the support structure, preferably to a temperature in a range from 300 to 600° C., additionally preferably in a range from 400 to 500° C.

According to a particular embodiment of the process according to the invention, the dehydration step is carried out in the gas phase. It is possible here to employ conventional apparatuses as are known to the skilled worker in the field of gas-phase reaction, for example tubular reactors. Particular preference is given to employing shell-and-tube heat exchangers and reactors which comprise thermoplates as heat exchangers.

According to one embodiment of the gas-phase dehydration reaction, pure 2-hydroxyisobutyric acid is introduced into a reactor comprising one of the above-mentioned fixed-bed catalysts. According to another embodiment, 2-hydroxyisobutyric acid is introduced into the reactor in the form of an aqueous solution comprising from 2 to 80% by weight, particularly preferably 5 to 50% by weight and additionally preferably 10 to 25% by weight of 2-hydroxyisobutyric acid, in each case based on the total weight of the aqueous solution. The pressure and temperature conditions inside the reactor are chosen such that the 2-hydroxyisobutyric acid, or the aqueous solution, is in the gaseous form when entering the reactor. Dehydration in the gas phase is preferably carried out at temperatures in the range of between 200 and 400° C., particularly preferably between 250 and 350° C. The pressure inside the reactor for gas-phase dehydration is preferably in a range from 0.1 to 50 bar, particularly preferably in a range from 0.2 to 10 bar and most preferably in a range from 0.5 to 5 bar.

For gas-phase dehydration, the amount of 2-hydroxyisobutyric acid introduced into the reactor is preferably in a range from 10 to 100% by volume, particularly preferably in a range from 20 to 100% by volume and most preferably in a range from 30 to 100% by volume.

According to another particular embodiment of the process according to the invention, the dehydration step is performed in the liquid phase. Liquid-phase dehydration may also be carried out in any apparatus known to the skilled worker, which enables a fluid to be heated to a desired reaction temperature, it being possible for the apparatus to be pressurized sufficiently so as to keep the reaction components in the liquid state under the desired temperature conditions.

According to a particular embodiment of the process according to the invention, the process of liquid-phase dehydration comprises a first step, in which pure 2-hydroxyisobutyric acid or an aqueous solution comprising from 5 to 100% by weight, especially preferably 20 to 100% by weight and most preferably 50 to 100% by weight, of 2-hydroxyisobutyric acid, based on the total weight of the aqueous solution, is introduced into a reactor. The pressure and temperature conditions inside the reactor are chosen such that said 2-hydroxyisobutyric acid, or said aqueous solution, is in the liquid form when entering the reactor. According to a particular embodiment of the process according to the invention in which a dehydration step is carried out in the liquid phase, 2-hydroxyisobutyric acid, or the aqueous solution, is passed over a fixed-catalyst bed inside the dehydration reactor in such a way that the liquid phase trickles over the surface of the catalyst particles. Such a procedure may be carried out for example in a trickle-bed reactor.

Dehydration in the liquid phase is carried out at temperatures preferably in the range of between 200 and 350° C., particularly preferably between 250 and 300° C. The pressure inside the reactor for liquid-phase dehydration is preferably in a range from 1 to 50 bar, particularly preferably in a range from 2 to 25 bar and most preferably in a range from 3 to 10 bar.

Catalysis of both gas-phase dehydration and liquid-phase dehydration may be carried out homogeneously or heterogeneously.

In the case of homogeneous catalysis, the catalyst which here preferably takes the form of an inorganic acid such as, for example, phosphoric acid or sulphuric acid is first brought into contact with pure 2-hydroxyisobutyric acid or with the aqueous solution comprising 2-hydroxyisobutyric acid. Thereafter, the resulting composition is introduced into the reactor and converted to methacrylic acid under the desired pressure and temperature conditions. It is also feasible to introduce the inorganic acid into the reactor independently of 2-hydroxyisobutyric acid or the aqueous solution. In this case, the reactor features at least two feed lines, one for 2-hydroxyisobutyric acid, or the aqueous solution comprising 2-hydroxyisobutyric acid, and one for the catalyst. If the dehydration reaction is carried out in the liquid phase in a trickle-bed reactor, preference is given to introducing the catalyst together with said 2-hydroxyisobutyric acid, or said aqueous solution comprising 2-hydroxyisobutyric acid, at the top of the reactor.

In the case of heterogeneous catalysis, the catalyst is in the form of a solid substrate located in the reaction space, for example in the form of a fixed bed, in the form of catalyst-coated plates, preferably thermoplates, which are arranged inside the reactor, or else in the form of catalyst-coated reactor walls. Possible reactors are described in DE-A-198 48 208, DE-A-100 19 381 and EP-A-I 234 612, for example. In the case of heterogeneous catalysis, preferred catalysts are support structures brought into contact with inorganic acids, preferably impregnated porous support structures. 2-Hydroxyisobutyric acid, or the aqueous solution comprising 2-hydroxyisobutyric acid, is then brought into contact with the surface of the solid catalyst material, either in the form of a vapour or in the form of a liquid.

According to a particularly preferred embodiment of the process according to the invention, dehydration of 2-hydroxyisobutyric acid is carried out in liquid phase at a pressure in a range from 200 to 500 mbar, at a temperature in a range from 160 to 300° C., preferably from 200 to 240° C. and in the presence of alkali metal ions as the catalyst.

Under the present reaction conditions, the methacrylic acid produced may be distilled off in the gaseous form together with water and then condensed in the form of an aqueous solution to possibly give an aqueous methacrylic acid solution which does not contain any catalyst components.

According to a particular embodiment of the process of the invention, the solution of methacrylic acid obtained in this way may be esterified without further work-up, where appropriate. This involves bringing said methacrylic acid solution into contact with appropriate alcohols and suitable esterification catalysts known to the skilled worker, such as concentrated acids, with heating, thereby converting said methacrylic acid to the corresponding esters.

Preferred alcohols are, inter alia, alcohols which in each case have at least one carbon atom, preferably from 2 to 12, and particularly preferably 4 to 9, carbon atoms. The structure of said alcohols may be linear, branched or cyclic. The alcohols may further comprise aromatic groups or substituents, for example halogen atoms. Preferred alcohols are in particular methanol, ethanol, n-propanol, isopropanol, n-butanol, 1-methylpropanol, 2-methylpropanol, tert-butanol, n-pentanol, 1-methylbutanol, 2-methylbutanol, 3-methylbutanol, 2,2-dimethyl-propanol, n-hexanol, 1-methylpentanol, 2-methylpentanol, 3-methylpentanol, 4-methylpentanol, 1,1-dimethylbutanol, 2,2-dimethylbutanol, 3,3-dimethylbutanol, 1,2-dimethylbutanol, n-heptanol, 1-methylhexanol, 2-methylhexanol, 3-methylhexanol, 4-methylhexanol, 1,2-dimethylpentanol, 1,3-dimethylpentanol, 1,1-dimethylpentanol, 1,1,2,2-tetramethylpropanol, benzyl alcohol, n-octanol, 2-ethylhexanol, n-nonanol, 1-methyloctanol, 2-methyloctanol, n-decanol, n-undecanol, 1-methyldecanol, 2-methyldecanol, n-dodecanol, 2,4-diethyloctanol, cyclopentanol, cyclohexanol, 4-tert-butylcyclohexanol, cycloheptanol, cyclododecanol, 2-(dimethylamino)ethanol, 3-(dimethylamino)propanol, 4-(dimethylamino)butanol, 5-(dimethylamino)pentanol, 6-(dimethylamino)hexanol, 8-(dimethylamino)octanol, 10-(dimethylamino)decanol, 12-(dimethylamino)dodecanol, 2-(diethylamino)ethanol, 3-(diethylamino)propanol, 4-(diethylamino)butanol, 5-(diethylamino)pentanol, 6-(diethylamino)hexanol, 8-(diethylamino)octanol, 10-(diethylamino)decanol, 12-(diethylamino)dodecanol, 2-(diisopropylamino)ethanol, 3-(diisopropylamino)propanol, 4-(diisopropylamino)butanol, 5-(diisopropylamino)pentanol, 6-(diisopropylamino)hexanol, 8-(diisopropylamino)octanol, 10-(diisopropylamino)decanol, 12-(diisopropylamino)dodecanol, 2-(dibutylamino)ethanol, 3-(dibutylamino)propanol, 4-(dibutylamino)butanol, 5-(dibutylamino)pentanol, 6-(dibutylamino)hexanol, 8-(dibutylamino)octanol, 10-(dibutylamino)decanol, 12-(dibutylamino)dodecanol, 2-(dihexylamino)ethanol, 3-(dihexylamino)propanol, 4-(dihexylamino)butanol, 5-(dihexylamino)pentanol, 6-(dihexylamino)hexanol, 8-(dihexylamino)octanol, 10-(dihexylamino)decanol, 12-(dihexylamino)dodecanol, 2-(methylethylamino)ethyl, 2-(methylpropylamino)ethanol, 2-(methylisopropylamino)ethanol, 2-(methylbutylamino)ethanol, 2-(methylhexylamino)ethanol, 2-(methyloctylamino)ethanol, 2-(ethylpropylamino)ethanol, 2-(ethylisopropylamino)ethanol, 2-(ethylbutylamino)ethanol, 2-(ethylhexylamino)ethanol, 2-(ethyloctylamino)ethanol, 3-(methylethylamino)propanol, 3-(methylpropylamino)propanol, 3-(methylisopropylamino)propanol, 3-(methylbutylamino)propanol, 3-(methylhexylamino)propanol, 3-(methyloctylamino)propanol, 3-(ethylpropylamino)propanol, 3-(ethylisopropylamino)propanol, 3-(ethylbutylamino)propanol, 3-(ethylhexylamino)propanol, 3-(ethyloctylamino)propanol, 4-(methylethylamino)butanol, 4-(methylpropylamino)butanol, 4-(methylisopropylamino)butanol, 4-(methylbutylamino)butanol, 4-(methylhexylamino)butanol, 4-(methyloctylamino)butanol, 4-(ethylpropylamino)butanol, 4-(ethylisopropylamino)butanol, 4-(ethylbutylamino)butanol, 4-(ethylhexylamino)butanol, 4-(ethyloctylamino)butanol, 2-(N-piperidinyl)ethanol, 3-(N-piperidinyl)propanol, 4-(N-piperidinyl)butanol, 5-(N-piperidinyl)pentanol, 6-(N-piperidinyl)hexanol, 8-(N-piperidinyl)octanol, 10-(N-piperidinyl)decanol, 12-(N-piperidinyl)dodecanol, 2-(N-pyrrolidinyl)ethanol, 3-(N-pyrrolidinyl)propanol, 4-(N-pyrrolidinyl)butanol, 5-(N-pyrrolidinyl)pentyl-, 6-(N-pyrrolidinyl)hexanol, 8-(N-pyrrolidinyl)octanol, 10-(N-pyrrolidinyl)decanol, 12-(N-pyrrolidinyl)dodecanol, 2-(N-morpholino)ethanol, 3-(N-morpholino)propanol, 4-(N-morpholino)butanol, 5-(N-morpholino)pentanol, 6-(N-morpholino)hexanol, 8-(N-morpholino)octanol, 10-(N-morpholino)decanol, 12-(N-morpholino)dodecanol, 2-(N'-methyl-N-piperazinyl)ethanol, 3-(N'-methyl-N-piperazinyl)propanol, 4-(N'-methyl-N-piperazinyl)butanol, 5-(N'-methyl-N-piperazinyl)pentanol, 6-(N'-methyl-N-piperazinyl)hexanol, 8-(N'-methyl-N-piperazinyl)octanol, 10-(N'-methyl-N-piperazinyl)decanol, 12-(N'-methyl-N-piperazinyl)dodecanol, 2-(N'-ethyl-N-piperazinyl)ethanol, 3-(N'-ethyl-N-piperazinyl)propanol, 4-(N'-ethyl-N-piperazinyl)butanol, 5-(N'-ethyl-N-piperazinyl)pentanol, 6-(N'-ethyl-N-piperazinyl)hexanol, 8-(N'-ethyl-N-piperazinyl)octanol, 10-(N'-ethyl-N-piperazinyl)decanol, 12-(N'-ethyl-N-piperazinyl)dodecanol, 2-(N'-isopropyl-N-piperazinyl)ethanol, 3-(N'-isopropyl-N-piperazinyl)propanol, 4-(N'-isopropyl-N-piperazinyl)butanol, 5-(N'-isopropyl-N-piperazinyl)pentanol, 6-(N'-isopropyl-N-piperazinyl)hexanol, 8-(N'-isopropyl-N-piperazinyl)octanol, 10-(N'-isopropyl-N-piperazinyl)decanol, 12-(N'-isopropyl-N-piperazinyl)dodecanol, 3-oxabutanol, 3-oxapentanol, 2,2-dimethyl-4-oxapentanol, 3,6-dioxaheptanol, 3,6-dioxaoctanol, 3,6,9-trioxadecanol, 3,6,9-trioxaundecanol, 4-oxapentanol, 4-oxahexanol, 4-oxaheptanol, 4,8-dioxanonanol, 4,8-dioxadecanol, 4,8-dioxaundecanol, 5-oxahexanol and 5,10-dioxaundecanol.

It is furthermore possible to use as solvents ethoxylated and/or propoxylated alcohols and also ethoxylated/propoxylated mixed alcohols, in particular
$R^a$—(O—$CH_2$—$CH_2$)$_x$—OH or $R^a$—(O—CH($CH_3$)—$CH_2$)$_x$—OH, or $R^a$—(O—$CH_2$—CH($CH_3$))$_x$—OH, where $R^a$ is $C_1$-$C_{20}$-alkyl and x is an integer between 10 and 20, or ethoxylated and/or propoxylated amino alcohols, for example $R^b{}_2$N(—$CH_2$—$CH_2$—O)$_y$—H or $R^b{}_2$N(—CH($CH_3$)—$CH_2$—O)$_y$—H or $R^b{}_2$N(—$CH_2$CH($CH_3$)—O)$_y$—H, where y is an integer between 1 and 4. $R^b$ is an alkyl group having 1-6 carbon atoms, with the nitrogen being able to form together with the substituents $R^b$ a five- to six-membered ring. Where appropriate, the ring may further be substituted by one or more short-chain alkyl groups, for example methyl, ethyl or propyl.

However, it may be advantageous additionally to purify the methacrylic acid before esterification, it being possible to employ, in principle, any purification method known to the skilled worker that is customarily applied to purifying contaminated (meth)acrylic acid obtained by catalytic gas-phase oxidation of propylene.

If the dehydration reaction has been carried out in the gas phase, preference is given to first condensing the methacrylic acid to give an aqueous methacrylic acid solution. Here, any condensation process known to the skilled worker may be employed in principle, for example fractional condensation as described in WO-A-2004/035514, WO-A-03/014172 or EP-A-EP 1 163 201 or by total condensation as described in EP-A-0 695 736. It is also feasible to add additional solvents, in particular water, during the condensation process in order to absorb the methacrylic acid as completely as possible.

The aqueous methacrylic acid solution obtained after condensation, or else the aqueous methacrylic acid solution obtained with liquid-phase dehydration, can then be relieved of water and other contaminants in further purification steps. Here, it is possible first to remove the water by azeotrope distillation in the presence of an entrainer as described, for example, in DE-A-198 53 064. It is also feasible to employ high-boiling organic solvents for absorbing the methacrylic acid, as is disclosed for example in EP-A-0 974 574. In addition to these distillation methods, it is also possible to employ membranes for dehydration, as proposed for example in DE-A-44 01 405. It is furthermore feasible to employ crystallization methods for purifying the aqueous methacrylic acid solution recovered in the case of liquid-phase dehydration or obtained by condensation.

The methacrylic acid obtained after dehydration can be purified still further in further process steps. It is thus possible to remove high-boiling contaminants which are still present by further distillation steps. However, particular preference is given to further purifying the methacrylic acid obtained after dehydration by using crystallization methods, as described for example in DE-A-101 49 353.

The purified methacrylic acid obtained in this way may then be esterified, where appropriate.

A contribution to achieving the objects stated at the outset is furthermore made by a process for preparing methacrylic acid or methacrylic esters, comprising the steps of:

IIA) preparing polyhydroxyalkanoates containing 2-hydroxyisobutyric acid monomer units by the process described above, IIB) cleaving the polyhydroxyalkanoates containing 2-hydroxyisobutyric acid monomer units with production of 2-hydroxyisobutyric acid and, where appropriate, neutralizing the 2-hydroxyisobutyric acid and/or purifying the 2-hydroxyisobutyric acid, IIC) dehydrating the 2-hydroxyisobutyric acid with production of methacrylic acid and, where appropriate, esterifying the methacrylate or methacrylic acid.

A contribution to achieving the objects stated at the outset is also made by a process for preparing poly(methacrylic) acid or poly(methacrylic) esters, comprising the steps of IIIA) preparing methacrylic acid by the process described above, IIIB) free-radical polymerization of the methacrylic acid, wherein, where appropriate, the methacrylic acid carboxyl groups may be esterified at least partially prior to or after the free-radical polymerization.

Figure 2:
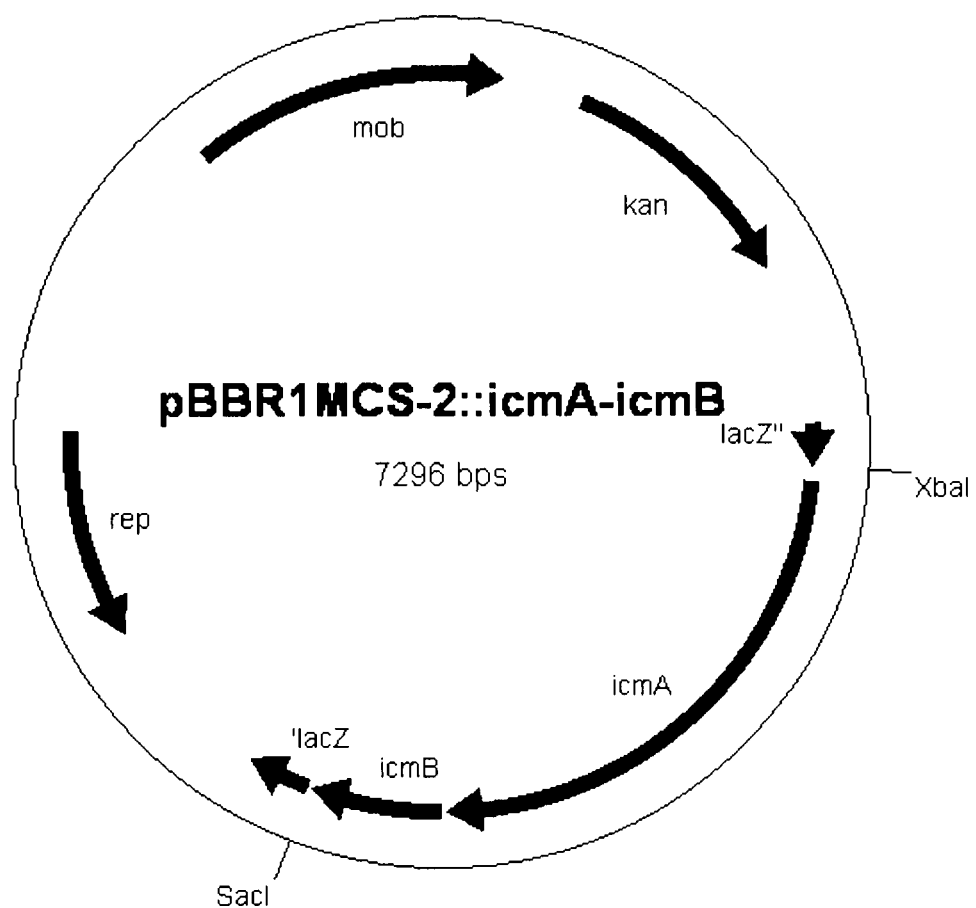
Figure 3:
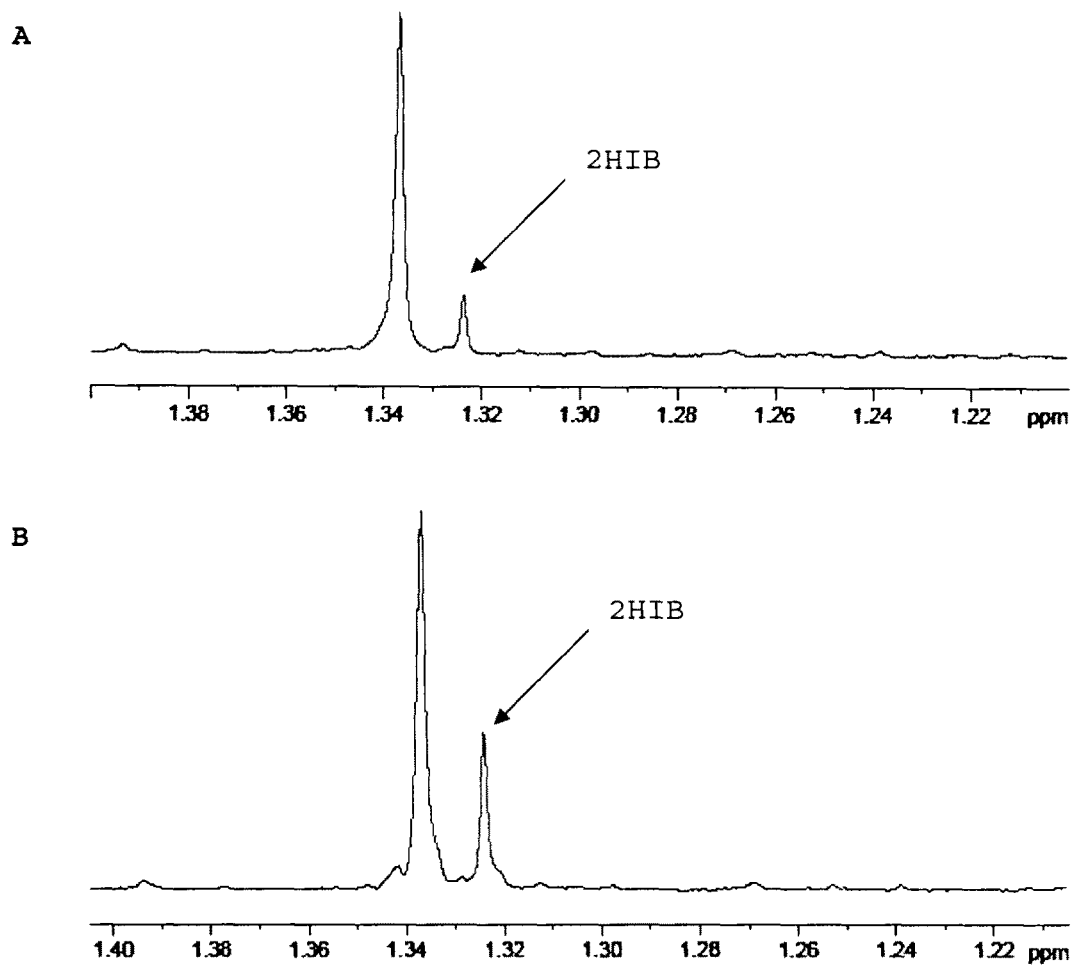
Figure 4A:
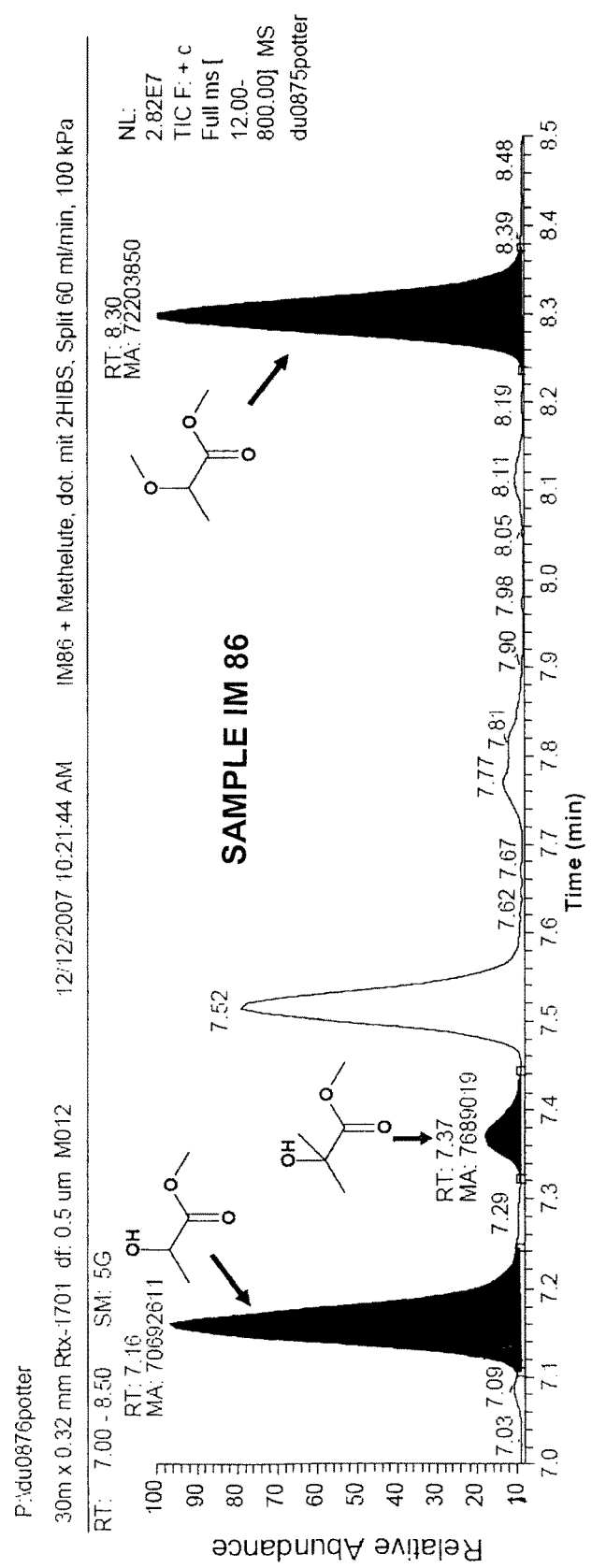
Figure 4B:
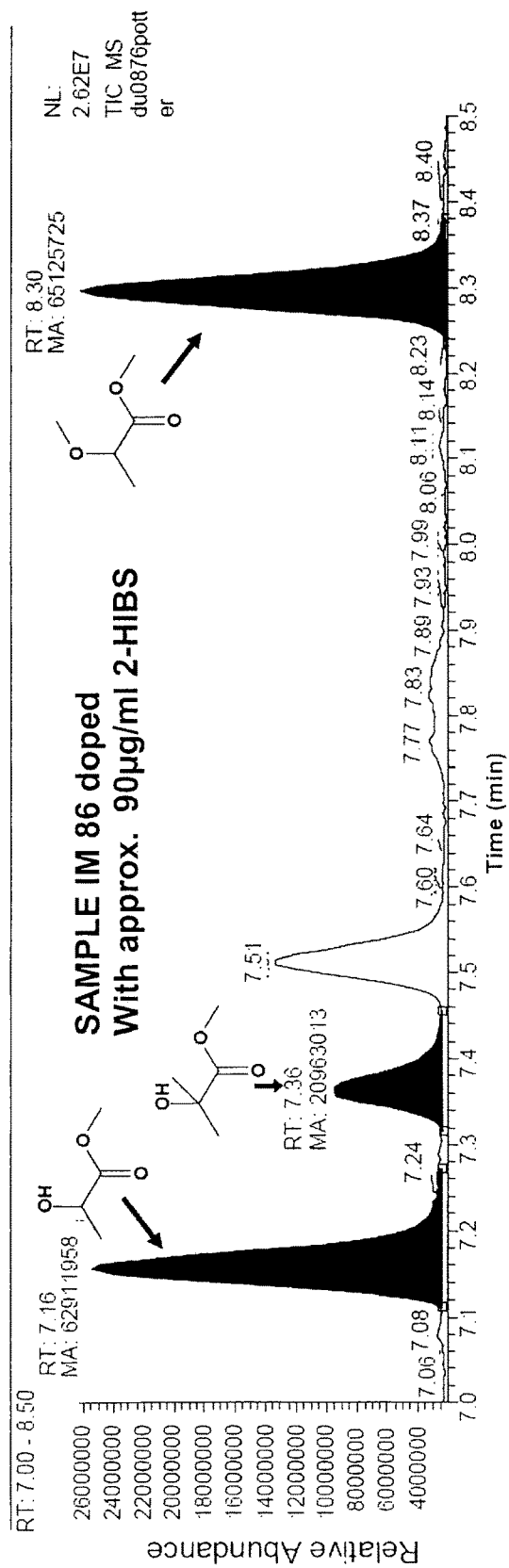

The present invention is described by way of example in the examples hereinbelow and is not intended to be limited to the embodiments mentioned in said examples, with its range of applications arising from the entire description and the claims. The following figures are part of the examples:

FIG. 1: hybrid plasmid pET101/D-TOPO::icmA-icmB;

FIG. 2: hybrid plasmid pBBR1MCS-2::icmA-icmB;

FIG. 3: 2-hydroxyisobutyric acid in the sample IM-86 was quantified after doping the sample with 2-hydroxyisobutyric acid. The methyl lactate peak (Rt. 7.16 min) was used as internal standard. The figure depicts the GC-MS chromatograph sections of the doped and original samples;

FIG. 4: addition of 2-hydroxyisobutyric acid to the sample IM-89. The figure depicts sections of the NMR spectra of the original sample (A) and of the doped sample (B).

EXAMPLES

1. Isolation of Genomic DNA and Amplification of Fragments icmA and icmB

Genomic DNA was isolated from the strain *Aquincola tertiaricarbonis* (*A. tertiaricarbonis* DSMZ 18512) using the DNeasy Blood & Tissue kit (Qiagen GmbH, Hilden, Germany) according to the manufacturer's information and used as template in a PCR for amplification of fragments icmA (1.7 kbp; DQ436456) and icmB (0.4 kbp; DQ436457) which code for an enzyme $E_3$. The oligonucleotides Aqt-icmA_fw 5'-CACC<u>ATG</u>ACCTGGCTTGAGCCGCAG-3' (SEQ ID NO: 3) (forward primer; start codon is underlined) and Aqt-icmA-Hind_rev 5'-AAAA<u>AAGCTT</u>CCTGC<u>TCA</u>GAAGACCGGCGTCTCGCG-3' (SEQ ID NO: 4) (reverse primer; stop codon and HindIII cleavage site are underlined) are used for amplification of icmA, and the oligonucleotides Aqt-icmB-Hind_fw 5'-AAAA<u>AAGCTT</u>CCCACC<u>ATG</u>GACCAAATCCCGATCCGC-3' (SEQ ID NO: 5) (forward primer; start codon and HindIII cleavage site are underlined) and Aqt-icmB_rev 5'-<u>TCA</u>GCGGGCGCCGCGCGCGGCGAC-3' (SEQ ID NO: 6) (reverse primer; stop codon is underlined) are used for amplification of icmB.

The polymerase chain reaction (PCR, according to SAIKI et al., 1985, Enzymatic amplification of β-globin genomic sequences and restriction site analysis for diagnosis of sickle cell anemia. Science 230:1350-1354.) mixture included the Pfu polymerase (Promega, Madison, USA). The PCR was carried out by way of 35 cycles of in each case 60 seconds at 95° C., 30 seconds at 65° C. and 4 minutes at 72° C. in a thermocycler (Primus 96 advanced; PEQLAB Biotechnologie GMBH, Erlangen, Germany).

The fragments were purified using the QIAquick PCR Purification Kit (Qiagen GmbH, Hilden) according to the manufacturer's information and then restricted by HindIII. Both mixtures were ligated via the HindIII cleavage site.

The ligation product icmA-icmB (2.1 kbp) was used as template for a Pfu-PCR using the oligonucleotides Aqt-icmA_fw 5'-CACC<u>ATG</u>ACCTGGCTTGAGCCGCAG-3' (SEQ ID NO: 7) (forward primer; start codon is underlined) and Aqt-icmB_rev 5'-<u>TCA</u>GCGGGCGCCGCGCGCGGCGAC-3' (SEQ ID NO: 8) (reverse primer; stop codon is underlined) (35 cycles of in each case 60 seconds at 95° C., 30 seconds at 65° C. and 4.5 minutes at 72° C.). The resulting PCR product of the corresponding size was purified using the QIAquick PCR Purification Kit (Qiagen GmbH, Hilden) according to the manufacturer's information.

2. Preparation of a *Ralstonia eutropha* Expression Vector

The purified PCR fragment icmA-icmB (2.1 kbp) was ligated into the vector pET101/D-TOPO (Invitrogen GmbH, Karlsruhe, Germany) according to the manufacturer's information. The resulting hybrid plasmid pET101/D-TOPO::icmA-icmB (FIG. 1, Seq. ID No. 1) was transferred into competent *E. coli* DH5α cells (New England Biolabs, Frankfurt, Germany) and checked by restriction and sequencing.

To obtain expression in *R. eutropha* strains, the wild types of which have activities of enzymes $E_1$, $E_2$ and $E_4$, the construct had to be cloned into a suitable broad host-range vector. The vector used is pBBR1MCS-2, described in KOVACH et al. (1995). Four new derivatives of the broad-host-range cloning vector pBBR1MCS carrying different antibiotic-resistance cassettes. Gene, 166:175-176.

For this purpose, the plasmids pET101/D-TOPO::icmA-icmB and pBBR1MCS-2 were restricted by the enzymes XbaI and SacI and the icmA-icmB fragment was ligated into the pBBR1MCS-2 target vector, and competent *E. coli* DH5α cells (New England Biolabs, Frankfurt) were transformed with the resultant hybrid plasmid, pBBR1MCS-2::icmA-icmB (FIG. 2, Seq. ID No. 2).

The plasmid was checked by restriction and sequencing and transferred into competent *E. coli* S17-1 cells, a strain which makes possible the conjugative transfer of plasmids into, inter alia, *Ralstonia eutropha* strains. For this purpose, spot-mating conjugation (as described in FRIEDRICH et al., 1981, Naturally occurring genetic transfer of hydrogen-oxidizing ability between strains of *Alcaligenes eutrophus*. J Bacteriol 147:198-205) was carried out, with *E. coli* S17-1 pBBR1MCS-2::icmA-icmB as donor and *R. eutropha* H16 (re-classified as *Cupriavidus necator*, DSMZ 428) and *R. eutropha* PHB-4 (re-classified as *Cupriavidus necator*, DSMZ 541) as recipient.

Transconjugants were obtained which harbour the pBBR1MCS-2::icmA-icmB plasmid.

3. Production of 2-hydroxyisobutyric Acid in Recombinant *R. eutropha* Cells Production of 2-hydroxyisobutyric acid was studied by growing the plasmid-harbouring *R. eutropha* strains described in example 2 in 50 ml Vollbrecht-MSM medium ((NH$_4$)$_2$HPO$_4$, 2.0 g; KH$_2$PO$_4$, 2.1 g; MgSO$_4$.7H$_2$O, 0.2 g; FeCl$_3$.6H$_2$O, 6 mg; CaCl$_2$.2H$_2$O, 10 mg; trace element solution (Pfennig and Lippert, 1966), 0.1 ml).

Additionally, the medium was supplemented with sodium gluconate (15 g/l), kanamycin (50 µg/ml) and coenzyme B12 (60 µg/ml). The cells were incubated on a thermostatted shaker at 30° C. and 160 rpm. After 30 h more sodium gluconate (1.5%, w/v) and coenzyme B12 [60 µg/ml] were fed in. The culture was harvested by centrifugation at 5000 rpm (4° C.) after 52 h. The culture supernatant was stored at −20° C. until analysis.

Detection and quantification of 2-hydroxyisobutyric acid were carried out by means of quantitative $^1$H-NMR spectrometry. The samples were concentrated quantitatively. $^1$H-NMR spectra of the residue were recorded and the content was calculated based on TSP (trisilylpropionic acid) as internal standard. The spectrum of 2-hydroxyisobutyric acid depicts a singlet at approx. 1.36 ppm, and pure 2-hydroxyisobutyric acid was added to the residue for validation (FIG. 3).

2-Hydroxyisobutyric acid concentrations of up to 0.72 mmol/kg were detected in the samples analysed. In contrast, no 2-hydroxyisobutyric acid was detected in corresponding control mixtures containing empty plasmid. The NMR measurements were confirmed quantitatively and qualitatively by means of GC-MS and addition of the pure 2-hydroxyisobutyric acid (FIG. 4). In this case, chromatographic separation was carried out on a 30 m Rtx-1701 capillary column (Fisher Scientific, Pittsburgh, USA). After lyophilization, the samples were resuspended using the derivatization reagent "Methelute" (Pierce, Rockford, USA). 0.5 µl of this solution was applied directly through a split/splitless injector. The 2-hydroxyisobutyric acid peaks were identified by comparing the mass spectrum with database spectra. The 2-hydroxyisobutyric acid content was estimated by doping the samples with a defined amount of the comparative substance, 2-hydroxyisobutyric acid. Concentrations of up to 44 µg/ml were detected in the samples analysed. No 2-hydroxyisobutyric acid was detected in control mixtures containing empty plasmid. Similarly, it was possible to detect 2-hydroxyisobutyric acid synthesized starting from fructose as carbon source (1.50, w/v).

4. Dehydration of 2-Hydroxyisobutyric Acid to Give Methacrylate

To 5 ml of a solution of 2-hydroxyisobutyric acid (0.2 g/l) produced according to example 3, NaOH (0.06 mg) is added with stirring. The solution is incubated with stirring and cooling with reflux at 185-195° C. under reduced pressure (300 torr). A further 0.5 mg of 2-hydroxyisobutyric acid in 5 ml is added every hour over a period of 5 h, said solution containing 0.4 percent by weight of p-methoxyphenol to prevent methacrylate from polymerizing. The reaction is stopped after 24 h of incubation. More than 90% of 2-hydroxyisobutyric acid are converted to methacrylate. Methacrylic acid is removed by distillation from the reaction mixture.

---

The invention claimed is:

1. A process tor preparing 2-hydroxyisobutyric acid, the process comprising:
   a-1) providing a 3-hydroxybutryrate producing microorganism wherein said microorganism is a mutant of a microorganism which has an activity of an enzyme $E_4$ which is a polyhydroxyalkanoate synthase capable of catalyzing the conversion of 3-hydroxylbutyryl-coenzyme A to polyhydroxybutyrate wherein said mutant lacks activity of enzyme $E_4$
   a-2) transforming said 3-hydroxybutryrate producing microorganism with a nucleic acid encoding a mutase having at least 95% amino acid sequence identity to the amino acid sequence encoded by the *Aquincola tertiaricarbonis* icmA and icmB wild type genes to obtain transformed cells comprising overexpressed enzyme $E_3$ which catalyzes the conversion of 3-hydroxylbutyryl-coenzyme A to 2-hydroxyisobutyryl-coenzyme A,
   b) after the transforming in a-2), contacting the transformed cells with a nutrient medium including a carbon source under conditions where 2-hydroxyisobutyric acid is produced from the carbon source; and optionally,
   c) purifying the 2-hydroxyisobutyric acid from the nutrient medium,
   wherein the 3-hydroxybutyrate producing microorganism is selected from the group consisting of *Alcaligenes latus, Bacillus subtilis, Methylobacterium extorquens, Ralstonia eutropha, Rhodospirillum rubrum, Rhodobacter sphaeroides, Paracoccus versutus, Pseudomonas aeruginosa, Pseudomonas putida*, and *Acinetobacter calcoaceticus*.

2. A process for preparing methacrylic acid or a methacrylic ester, comprising:
   IA) preparing 2-hydroxyisobutyric acid by the process according to claim 1, and optionally purifying and/or neutralizing the 2-hydroxyisobutyric acid; and
   IB) dehydrating the 2-hydroxyisobutyric acid to obtain methacrylic acid, and optionally esterifying the methacrylic acid to obtain the methacrylic ester.

3. A process for preparing poly(methacrylic) acid or a poly(methacrylic) ester, comprising:
   IIIA) preparing methacrylic acid by a process according to claim 2; and
   IIIB) free-radical polymerizing the methacrylic acid,
   wherein carboxyl groups of the methacrylic acid are optionally esterified at least partially prior to or after the free-radical polymerization.

4. The process of claim 1, wherein a concentration of the 2-hydroxyisobutyric acid produced in the contacting in (b) is up to 44 µg/ml.

5. The process of claim 1, wherein the contacting in (b) is carried out under aerobic conditions.

6. The process of claim 1, wherein the process comprises the (c) purifying of the 2-hydroxyisobutyric acid from the nutrient medium.

7. The process of claim 1, wherein the process does not comprise the (c) purifying of the 2-hydroxyisobutyric acid from the nutrient medium.

8. The process of claim 1, wherein the 3-hydroxybutryrate producing microorganism is *Ralstonia eutropha*.

9. The process of claim 1, further comprising:
   introducing air comprising oxygen into the nutrient medium,
   wherein the introducing of the air and the contacting in (b) are performed at the same time.

10. The process of claim 1,
    wherein the contacting in (b) is carried out under aerobic conditions for at least 30 hours.

11. The process of claim 1, wherein the 3-hydroxybutryrate producing microorganism transformed in a-2) is *Ralstonia eutropha* PHB-4.

* * * * *